(12) United States Patent
Yamamoto

(10) Patent No.: US 7,267,824 B2
(45) Date of Patent: *Sep. 11, 2007

(54) MULTI-SUBTYPE FIV VACCINES

(75) Inventor: Janet K. Yamamoto, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 315 days.

This patent is subject to a terminal disclaimer.

(21) Appl. No.: 10/408,701

(22) Filed: Apr. 7, 2003

(65) Prior Publication Data

US 2003/0180327 A1 Sep. 25, 2003

Related U.S. Application Data

(63) Continuation of application No. 09/707,532, filed on Nov. 7, 2000, now Pat. No. 6,544,528, which is a continuation of application No. 09/025,610, filed on Feb. 18, 1998, now Pat. No. 6,254,872, which is a continuation of application No. PCT/US96/13580, filed on Aug. 23, 1996, and a continuation-in-part of application No. 09/512,746, filed on Oct. 1, 1997, now Pat. No. 6,447,993, which is a continuation of application No. 08/519,386, filed on Aug. 25, 1995, now abandoned.

(51) Int. Cl.
*A61K 39/21* (2006.01)

(52) U.S. Cl. .............. 424/207.1; 424/204.1; 424/208.1; 435/320.1

(58) Field of Classification Search ............ 424/208.1, 424/204.1, 207.1, 184.1; 435/6, 320.1
See application file for complete search history.

(56) References Cited

U.S. PATENT DOCUMENTS

| | | | |
|---|---|---|---|
| 5,037,753 A | 8/1991 | Pederson et al. | |
| 5,118,602 A | 6/1992 | Pederson et al. | |
| 5,275,813 A | 1/1994 | Yamamoto et al. | |
| 5,510,106 A | 4/1996 | Yamamoto et al. | |
| 5,846,825 A | 12/1998 | Yamamoto | |
| 6,107,077 A | 8/2000 | Yamamoto | |
| 6,254,872 B1 * | 7/2001 | Yamamoto | 424/207.1 |
| 6,447,993 B1 * | 9/2002 | Yamamoto | 435/5 |
| 6,544,528 B1 * | 4/2003 | Yamamoto | 424/208.1 |

FOREIGN PATENT DOCUMENTS

| | | |
|---|---|---|
| WO | 9301278 | 1/1993 |
| WO | 9420622 | 9/1994 |
| WO | 9630045 | 10/1996 |

OTHER PUBLICATIONS

Yamamoto et al., Development of the dual sub-type feline immunodeficiency virus vaccine, AIDScience, Apr. 26, 2002, vol. 2, No. 8. (http://www.aidscience.org/Articles/aidscience020.htm)*

Pedersen, N.C. et al. (1987) "Isolation of a T-Lymphotropic Virus from Domestic Cats with an Immunodeficiency-Like Syndrome" *Science* 235:790-793.
Yamamoto, J.K. et al. (1988) "Feline Immunodeficiency Syndrome—A Comparison between Feline T-Lymphotropic Lentivirus and Feline Leukemia Virus" *Leukemia* 2(12):204S-215S.
Yamamoto, J.K. et al. (1988) "Pathogenesis of experimentally induced feline immunodeficiency virus infection in cats" *American Journal of Veterinary Research* 49(8):1246-1258.
Ackley, C.D. et al. (1990) "Immunologic Abnormalities in Pathogen-Free Cats Experimentally Infected with Feline Immunodeficiency Virus" *Journal of Virology* 64(11):5652-5655.
Olmsted, R.A. et al. (1989) "Molecular cloning of feline immunodeficiency virus" *Proc. Natl. Acad. Sci. USA* 86:2448-2452.
Olmsted, R.A. et al. (1989) "Nucleotide sequence analysis of feline immunodeficiency virus: Genome organization and relationship to other lentiviruses" *Proc. Natl. Acad. Sci. USA* 86:8088-8092.
Talbott, R.L. et al. (1989) "Nucleotide sequence and genomic organization of feline immunodeficiency virus" *Proc. Natl. Acad. Sci. USA* 86:5743-5747.
Hosie, M.J., Jarrett, O. (1989) "Serological responses of cats to feline immunodeficiency virus" *AIDS* 4(3):215-220.
Hosie, M.J. et al. (1995) "Protection against Homologous but Not Heterologous Challenge Induced by Inactivated Feline Immunodeficiency Virus Vaccines" *Journal of Virology* 69(2):1253-1255.
Sodora, D.L. et al. (1994) "Identification of Three Feline Immunodeficiency Virus (FIV) env Gene Subtypes and Comparision of the FIV and Human Immunodeficiency Virus Type 1 Evolutionary Patterns" *Journal of Virology* 68(4):2230-2238.
Kakinuma, S. et al. (1995) "Nucleotide Sequence of Feline Immunodeficiency Virus: Classification of Japanese Isolates into Two Subtypes Which Are Distinct from Non-Japanese Subtypes" *Journal of Virology* 69(6):3639-3646.
Johnson, C.M. et al. (1994) "FIV as a Model for AIDS Vaccination" *AIDS Research and Human Retroviruses* 10(3):225-228.
Yamamoto, J.K. et al. (1993) "Experimental Vaccine Protection against Homologous and Heterologous Strains of Feline Immunodeficiency Virus" *Journal of Virology* 67(1):601-605.
Yamamoto, J.K. et al. (1991) "Experimental Vaccine Protection Against Feline Immunodeficiency Virus" *AIDS Research and Human Retroviruses* 7(11):911-922.
Yamamoto, J.K. et al. (1991) "Development of IL-2-Independent Feline Lymphoid Cell Lines Chronically Infected with Feline Immunodeficiency Virus: Importance for Diagnostic Reagents and Vaccines" *Intervirology* 32:361-375.

(Continued)

*Primary Examiner*—Stacy B. Chen
(74) *Attorney, Agent, or Firm*—Saliwanchik, Lloyd & Saliwanchik

(57) ABSTRACT

The subject invention pertains to novel methods and compositions for protecting cats from infection by a broad range of FIV strains using a multi-subtype FIV vaccine. Multi-subtype FIV vaccines comprising either cell free whole virus or cell lines infected with viruses are described. Methods for vaccinating cats with the subject vaccine compositions are also described. Cats vaccinated according to the methods and compositions of the subject invention exhibit protective humoral and cellular immune responses to FIV when challenged with homologous or heterologous strains of FIV. The subject invention also pertains to novel feline cell lines that are susceptible to infection by FIV and their methods of use.

70 Claims, 6 Drawing Sheets

OTHER PUBLICATIONS

Figure 1:
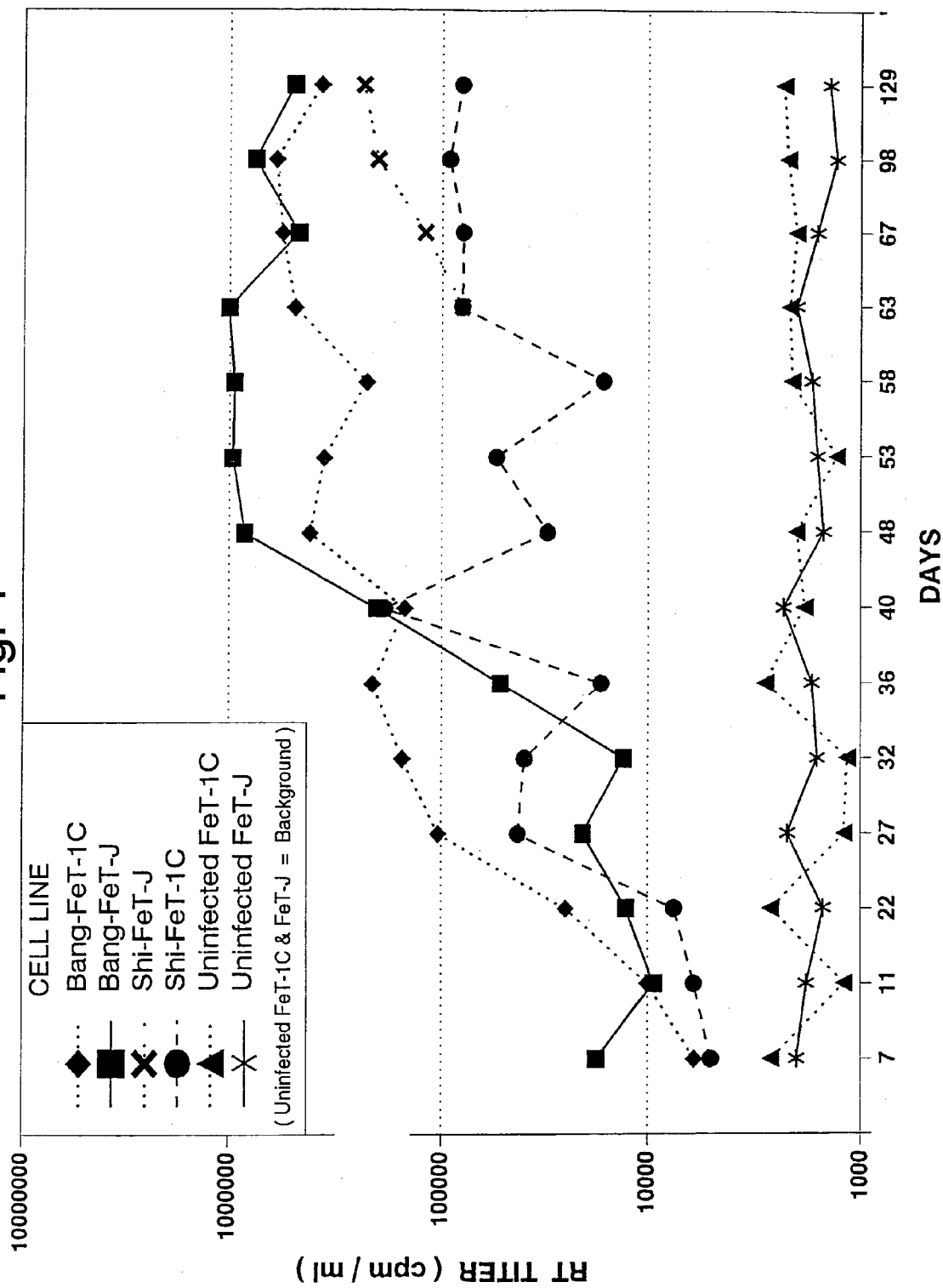

Rigby, M.A. et al. (1993) "Evolution of structural proteins of feline immunodeficiency virus: molecular epidemiology and evidence of selection for change" *Journal of General Virology* 74:425-436.

Murphy, F.A., Kingsbury, D.W. (1990) "Virus Taxonomy" *Virology*, 2nd edition, Raven Press Ltd. New York, New York.

Louwagie, J. et al. (1993) "Phylogenetic analysis of *gag* genes from 70 international HIV-1 isolates provides evidence for multiple genotypes" *AIDS* 7(6):769-780.

Okada, S. et al. (1994) "Superinfection of Cats with Feline Immunodeficiency Virus Subtypes A and B" *AIDS Research and Human Retroviruses* 10(12):1739-1746.

Satoshi, Nagata et al. (1989) Establishment of FIV-Producing Cell Lines from FIV Seropositive Cats V International Conference on AIDS, The Scientific and Social Challenge, XP-000972975, abstract only, p. 598.

\* cited by examiner

IMMUNIZATION

IMMUNIZATION

```
                           SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 1:
```

```
Gly Ser Trp Phe Arg Ala Ile Ser Ser Trp Lys Gln Arg Asn Arg Tr
1               5                   10                  15

Glu Trp Arg Pro Asp Phe
            20
```

(2) INFORMATION FOR SEQ ID NO: 2:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

```
Gln Glu Leu Gly Cys Asn Gln Asn Gln Phe Phe Cys Lys Ile
1               5                   10
```

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

GAAATGTATA ATATTGCTGG                                      20

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GAATTGATTT TGATTACATC C                                    21

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

TAGTAGTTAT AGTGGTACTA                                      20

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

TCTTTAAGGC TTCAGTCACC T                                              21

(2) INFORMATION FOR SEQ ID NO: 7:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 7:

GTACAAATAG TAGTAGTACA A                                              21

(2) INFORMATION FOR SEQ ID NO: 8:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 8:

TCTTTAAGGC TTCAGTCACC T                                              21

(2) INFORMATION FOR SEQ ID NO: 9:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 9:

GGGACTACTA GCAATGGAAT A                                              21

(2) INFORMATION FOR SEQ ID NO: 10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 10:

AGTGCCTCAG TTATTTTATC C                                              21

(2) INFORMATION FOR SEQ ID NO: 11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 11:

TGGGACTGAT GATAGTAAAA C                                              21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

AGTGCCTCAG TTATTTTATC C                      21

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

TGGGACTGAT AATAGTGAAA C                      21

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

AGTGCCTCAG TTATTTATC C                       21

(2) INFORMATION FOR SEQ ID NO: 15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

TCATCATTTC CAACATGTC                        19

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

AATGCTTCAG TTATTTGATC                       20

MULTI-SUBTYPE FIV VACCINES

CROSS-REFERENCE TO RELATED APPLICATIONS

This application is a continuation of U.S. application Ser. No. 09/707,532, filed Nov. 7, 2000, now, U.S. Pat. No. 6,544,528, which is a continuation U.S. application Ser. No. 09/025,610, filed Feb. 18, 1998, now, U.S. Pat. No. 6,254,872, which is a continuation of International Application No. PCT/US96/13580, filed Aug. 23, 1996 and this application is a continuation-in-part of U.S. application Ser. No. 09/512,746, filed Oct. 1, 1997, now U.S. Pat. No. 6,447,993, which is a continuation of U.S. application Ser. No. 08/519,386, filed Aug. 25, 1995, now abandoned.

The subject invention was made with government support under a research project supported by National Institutes of Health Grant No. NIH AI30904. The government has certain rights in this invention.

BACKGROUND OF THE INVENTION

Domestic cats are subject to infection by several retroviruses, including feline leukemia virus (FeLV), feline sarcoma virus (FeSV), endogenous type C oncoronavirus (RD-114), and feline syncytia-forming virus (FeSFV). Of these, FeLV is the most significant pathogen, causing diverse symptoms including lymphoreticular and myeloid neoplasms, anemias, immune-mediated disorders, and an immunodeficiency syndrome that is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (now designated as feline immunodeficiency virus, FIV) was first reported in Pedersen et al. (1987). Characteristics of FIV have been reported in Yamamoto et al. (1988a); Yamamoto et al. (1988b); and Ackley et al. (1990). Seroepidemiologic data have shown that infection by FIV is indigenous to domestic and wild felines throughout the world. A wide variety of symptoms are associated with infection by FIV, including abortion, alopecia, anemia, conjunctivitis, chronic rhinitis, enteritis, gingivitis, hematochezia, neurologic abnormalities, periodontitis, and seborrheic dermatitis. The immunologic hallmark of domestic cats infected with FIV is a chronic and progressive depletion of feline $CD4^+$ peripheral blood lymphocytes, a reduction in the CD4:CD8 cell ratio and, in some cases, an increase in CD8-bearing lymphocytes. Based on molecular, biochemical and immunopathologic characteristics, FIV infection of cats is now considered to be a better feline AIDS model than FeLV-FAIDS.

Cloning and sequence analysis of FIV has been reported in Olmsted et al. (1989a); Olmsted et al. (1989b); and Talbott et al. (1989). Hosie and Jarret (1990) described the serological response of cats infected with FIV. FIV virus subtypes can be classified according to immunotype based on the level of cross-neutralizing antibodies elicited by each strain (Murphy and Kingsbury, 1990). Recently, viruses have been classified into subtypes according to genotype based on nucleotide sequence homology. Although HIV and FIV subtyping is based on genotype (Sodora et al, 1994; Rigby et al., 1993; and Louwagie et al., 1993), little is known about the correlation between the genotype and immunotype of subtypes. FIV viral isolates are currently classified into four FIV subtypes: A, B, C and D. (Kakinuma et al., 1995). Infectious isolates and infectious molecular clones have been described for all FIV subtypes except for subtype C (Sodora et al., 1994). Subtype C FIV has only been identified from cellular DNA of cats from Canada (Sodora et al., 1994; Rigby et al., 1993; Kakinuma et al., 1995).

A major difficulty in developing an FIV vaccine has been in identifying a vaccine approach that is effective against a broad range of FIV strains including field isolates from different subtypes or clades. Vaccine prophylaxis for FIV has been attained against homologous and slightly heterologous strains using a single-strain vaccine, but not against challenge with moderate to greatly heterologous strains (Johnson et al., 1994; Yamamoto et al., 1993). Thus, there remains a need for a vaccine that protects across multiple FIV subtypes.

BRIEF SUMMARY OF THE INVENTION

The subject invention concerns a vaccine that elicits a broad range of protective immunity against FIV infections in a host animal. Specifically, the subject invention concerns a multi-subtype FIV vaccine that is prepared using cell-free viral isolates from different FIV subtypes, or a combination of cell lines each infected with a different prototype FIV virus from a different subtype. Cats vaccinated with the FIV vaccines of the subject invention develop humoral and cellular immune responses to homologous and heterologous FIV strains.

The subject invention also concerns novel feline cell lines that are susceptible to infection by multiple FIV subtypes. The cell lines of the subject invention are useful for propagating and producing multiple FIV subtypes, as well as for use in FIV vaccines according to the methods of the subject invention. In addition, the cell lines can also be used in place of feline peripheral blood mononuclear cells (PBMC) in FIV viral neutralization assays of feline antisera.

BRIEF DESCRIPTION OF THE DRAWINGS

FIG. 1 shows the reverse transcriptase (RT) levels of $FIV_{Bang}$ and $FIV_{Shi}$ produced after infecting FeT-1C and FeT-J cell lines with these FIV strains.

FIG. 2 shows the immunoreaction of anti-FIV antibodies from dual-subtype vaccinated cats with FIV proteins as detected by immunoblot. The number over each blot represent the number of vaccinations received by the animal when the sera was tested.

FIG. 3 shows the immunoreaction of anti-FIV antibodies from triple-subtype vaccinated cats with FIV proteins as detected by immunoblot. The number over each blot represent the number of vaccinations received by the animal when the sera was tested.

FIG. 4 shows the immunoreactivity of anti-FIV antibodies from triple-subtype vaccinated cats with FIV SU-V3-2 peptide as detected by ELISA.

FIG. 5 shows the immunoreactivity of anti-FIV antibodies from triple-subtype vaccinated cats with FIV TM-C1 peptide as detected by ELISA.

FIG. 6 shows cross-neutralizing antibody titers of sera from cats infected with either $FIV_{Pet}$ ($A_P$), $FIV_{Dix}$ ($A_D$), $FIV_{UK8}$ ($A_U$), $FIV_{Bang}$ ($B_B$), $FIV_{Aom1}$ ($B_A$), and $FIV_{Shi}$ ($D_S$). Sera at pre-infection (column 1), 6 months post-infection (column 2), and 12 months post-infection (column 3) were tested against subtype A $FIV_{Pet}$, subtype B $FIV_{Bang}$, and subtype D $FIV_{Shi}$ in the FeT-1C-cell line. At least three cats per each strain were tested and results show VN titer from a representative cat from each strain. Similar results were obtained using primary PBMC for VN assay.

BRIEF DESCRIPTION OF THE SEQUENCES

SEQ ID NO. 1 is an amino acid sequence of an FIV surface envelope peptide designated as SV-V3-2.

SEQ ID NO. 2 is an amino acid sequence of an FIV transmembrane peptide designated as TM-C1.

SEQ ID NO. 3 is a nucleotide sequence of an FIV PCR primer.

SEQ ID NO. 4 is a nucleotide sequence of an FIV PCR primer.

SEQ ID NO. 5 is a nucleotide sequence of an FIV PCR primer.

SEQ ID NO. 6 is a nucleotide sequence of an FIV PCR primer.

SEQ ID NO. 7 is a nucleotide sequence of an FIV PCR primer.

SEQ ID NO. 8 is a nucleotide sequence of an FIV PCR primer.

SEQ ID NO. 9 is a nucleotide sequence of an FIV PCR primer.

SEQ ID NO. 10 is a nucleotide sequence of an FIV PCR primer.

SEQ ID NO. 11 is a nucleotide sequence of an FIV PCR primer.

SEQ ID NO. 12 is a nucleotide sequence of an FIV PCR primer.

SEQ ID NO. 13 is a nucleotide sequence of an FIV PCR primer.

SEQ ID NO. 14 is a nucleotide sequence of an FIV PCR primer.

SEQ ID NO. 15 is a nucleotide sequence of an FIV PCR primer.

SEQ ID NO. 16 is a nucleotide sequence of an FIV PCR primer.

DETAILED DISCLOSURE OF THE INVENTION

The subject invention concerns novel methods and vaccine compositions useful for inducing protective immunity to FIV infection in a susceptible host animal. The vaccine compositions described herein, when administered to a host animal, induce protective humoral and cellular immune responses against infection by homologous and heterologous strains of FIV. The vaccine compositions may comprise either cell-free FIV viral isolates or FIV-infected cell lines. In a preferred embodiment, the vaccine composition of the subject invention comprises FIV strains from two different FIV subtypes. Preferably, the vaccine composition comprises three FIV strains, each strain from a different FIV subtype. More preferably, at least one FIV strain from each of FIV subtype A, subtype B and subtype D is included in the vaccine composition.

In a specific embodiment, the vaccine composition comprises $FIV_{Pet}$- and $FIV_{Shi}$-infected cell lines. In another embodiment, the vaccine composition comprises $FIV_{Pet}$-, $FIV_{Bang}$-, and $FIV_{Shi}$-infected cell lines. The use of other FIV strains representative of all or a portion of FIV subtypes is specifically contemplated by the subject invention. For example, $FIV_{Dix}$ or $FIV_{UK8}$ could be included in the vaccine compositions in addition to or in place of $FIV_{Pet}$ for purposes of providing an FIV subtype A prototype virus. Similar additions or substitutions with other FIV strains could be made for FIV subtype B and D prototype viruses.

As described herein, the vaccine compositions of the subject invention may comprise cell-free whole FIV virus, or portions of the virus, FIV proteins and polypeptides, as well as FIV-infected cell lines, or a combination of cell-free virus and infected cell lines. Vaccine compositions comprising FIV-infected cell lines may comprise multiple cell lines, each infected with a different FIV subtype. The vaccine compositions of the subject invention also encompass recombinant viral vector-based FIV constructs that may comprise, for example, FIV env, gag/pro, or env-gag/pro. Any suitable viral vector that can be used to prepare recombinant vector/FIV constructs is contemplated for use with the subject invention. For example, viral vectors derived from adenovirus, avipox, feline herpesvirus, vaccinia, canarypox, entomopox, swinepox and others known in the art can be used with the compositions and methods of the present invention. Recombinant polynucleotide vectors that encode and express FIV components can be constructed using standard genetic engineering techniques known in the art. In addition, the various vaccine compositions described herein can be used separately and in combination with each other. For example, primary immunizations of an animal may use recombinant vector-based FIV constructs, having single or multiple subtype components, followed by secondary boosts with vaccine compositions comprising inactivated FIV-infected cell lines. Other immunization protocols with the vaccine compositions of the invention are apparent to persons skilled in the art and are contemplated within the scope of the present invention.

The multi-subtype FIV vaccines specifically described herein were tested for immunogenicity and efficacy in cats. Specific pathogen free (SPF) cats vaccinated with the subject vaccine compositions were monitored for humoral and cellular immune responses before and after challenge with homologous and heterologous FIV strains. Humoral responses were monitored by measuring viral neutralizing (VN) antibody activity and cellular responses were monitored by measuring cytotoxic T lymphocyte (CTL) activity. Sera and immunocytes from vaccinated cats were tested in vitro for VN and CTL activities, respectively, against homologous and heterologous FIV strains, and demonstrated that the vaccines can elicit broad-range protection from FIV infection. According to the teachings of the subject invention, by combining prototype virus isolates from different FIV subtypes, or by combining individual cells infected with prototype virus of different subtypes, an effective multi-subtype FIV vaccine can be produced.

All FIV strains, in addition to those specifically exemplified herein, are contemplated for use with the subject invention. A number of FIV isolates have been described in the literature and are known to those skilled in the art. $FIV_{Pet}$ has been described in U.S. Pat. No. 5,037,753. Other FIV isolates which have been described can be readily isolated from infected cats by persons of ordinary skill in the art using standard techniques. Methods for isolating and culturing FIV are described in U.S. Pat. Nos. 5,037,753 and 5,118,602, which are herein corporated by reference.

The novel cell lines exemplified herein can be used in the vaccine methods and compositions of the present invention. Other cells or cell lines that are susceptible to infection by FIV strains, including peripheral blood mononuclear cells, are also contemplated for use with the present invention.

Natural, recombinant or synthetic polypeptides of FIV viral proteins, and peptide fragments thereof, can also be used as vaccine compositions according to the subject methods. In a preferred embodiment, FIV polypeptides derived from multiple FIV subtypes are combined in a vaccine composition and are used to vaccinate a host animal. For example, polypeptides based on the FIV envelope glycoprotein from at least two prototype FIV strains from different subtypes can be combined in the vaccine. The polypeptides may be homologous to one strain or may comprise "hybrid" or "chimeric" polypeptides whose amino acid sequence is derived from joining or linking polypeptides from at least two distinct FIV subtypes. Procedures for preparing FIV polypeptides are well known in the art. For example, FIV polypeptides can be synthesized using solid-phase synthesis methods (Merrifield, 1963). FIV polypeptides can also be produced using recombinant DNA techniques wherein a polynucleotide molecule encoding an FIV protein or peptide is expressed in a host cell, such as bacteria, yeast, or mammalian cell lines, and the expressed protein purified using standard techniques of the art.

The present invention also concerns novel feline T-cell lines that are susceptible to infection by FIV. Both interleukin-2 (IL-2) dependent and independent cells are specifically exemplified. The cell lines designated as FeT-1C and FeT-J are described herein. The FeT-1C cell line is IL-2 dependent, whereas the FeT-J cell line is IL-2 independent. The cell lines of the subject invention are useful for providing a vehicle for FIV immunization of cats, as well as for propagating and producing FIV viral strains in vitro. Both the IL-2-dependent FeT-1C and IL-2-independent FeT-J uninfected cell lines were tested over 20 times for reverse transcriptase (RT) activity in culture fluids and for FIV proviral sequence by PCR and were confirmed negative for FIV. FeT-J cell line was highly infectable with all of the FIV strains tested, including $FIV_{Shi}$, $FIV_{Dix}$, $FIV_{UK8}$, $FIV_{Pet}$ and $FIV_{Bang}$ but was more difficult to directly infect with $FIV_{Shi}$.

The subject invention further concerns cellular products produced by the cell lines of the present invention. The cellular products can be isolated and detected using procedures known to the skilled artisan. Antibodies to the cell lines can also be produced using known methods and are contemplated by the subject invention.

The FIV uninfected cell lines designated as FeT-1C (ATCC Accession No. CRL 11968) and as FeT-J (ATCC Accession No. CRL 11967) were both deposited with the American Type Culture Collection, Rockville, Md. on Aug. 24, 1995. $FIV_{Bang}$-(ATCC Accession No. 11975) and $FIV_{Shi}$-(ATCC Accession No. 11976) infected cell lines were deposited with the American Type Culture Collection on Aug. 25, 1995.

The subject cultures have been deposited under conditions that assure that access to the culture will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

According to the methods of the subject invention, the FIV vaccine compositions described herein are administered to susceptible hosts, typically domestic cats, in an effective amount and manner to induce protective immunity against subsequent challenge or infection of the host by FIV. The vaccines are typically administered parenterally, by injection, for example, either subcutaneously, intraperitoneally, or intramuscularly. Other suitable modes of administration include oral or nasal administration. Usually, the vaccines are administered to a host at least two times, with an interval of one or more weeks between each administration. However, other regimens for the initial and booster administrations of the vaccine are contemplated, and may depend on the judgment of the practitioner and the particular host animal being treated.

The vaccine compositions of the subject invention can be prepared by procedures well known in the art. For example, the vaccines are typically prepared as injectables, e.g., liquid solutions or suspensions. The vaccines are administered in a manner that is compatible with dosage formulation, and in such amount as will be therapeutically effective and immunogenic in the recipient. The optimal dosages and administration patterns for a particular vaccine formulation can be readily determined by a person skilled in the art.

Virus and cells in a vaccine formulation may be inactivated or attenuated using methods known in the art. For example, whole virus and infected cells can be inactivated or attenuated by exposure to paraformaldehyde, formalin, phenol, UV light, elevated temperature and the like. The amount of cell-free whole FIV virus in a vaccine dose will usually be in the range from about 0.1 mg to about 5 mg, and more usually being from about 0.2 mg to about 2 mg. The dosage for vaccine formulations comprising FIV-infected cell lines will usually contain from about $10^6$ to about $10^8$ cells per dose, and more usually from about $5 \times 10^6$ to about $7.5 \times 10^7$ cells per dose.

Virus or cells were typically combined with an adjuvant just prior to administration. Adjuvants used in the vaccine formulations typically were either threonyl muramyl dipeptide (MDP) (Byars et al., 1987) or a combination of Freud's complete and incomplete adjuvants. A variety of other adjuvants suitable for use with the methods and vaccines of the subject invention, such as alum, are well known in the art and are contemplated for use with the subject invention.

The subject invention further concerns a novel method for assaying for virus neutralizing (VN) antibodies in a sample using the uninfected cell lines of the present invention. Unlike PBMC which expire after a limited number of passages and do not propagate as readily as FeT-1C or FeT-J cells, the FeT-1C and FeT-J cells are an established cell line and can be readily cryopreserved for future use. Results obtained from VN assays using FeT-1C cells are more highly reproducible than VN assays using PBMC because PBMC from different SPF cats have individual variability in cell growth rate and FIV infectability. Further, PBMC for VN assays have to be obtained from SPF cats which require germ-free housing and maintenance in order to eliminate possible in vivo infection which may affect an in vitro VN assay using PBMC. Thus, a feline cell line such as FeT-1C which can be readily infected with FIV of different subtypes can be advantageously substituted for PBMC in VN assays.

The following abbreviations of FIV strains are used herein:

| Strain (subtype) | Abbreviation |
|---|---|
| Petaluma (A) | $FIV_{Pet}$ |
| Dixon (A) | $FIV_{Dix}$ |
| UK8 (A) | $FIV_{UK8}$ |
| Bangston (B) | $FIV_{Bang}$ |
| Aomori-1 (B) | $FIV_{Aom1}$ |
| Aomori-2 (B) | $FIV_{Aom2}$ |
| Shizuoka (D) | $FIV_{Shi}$ |

All patents, patent applications, provisional applications, and publications referred to or cited herein are incorporated by reference in their entirety to the extent they are not inconsistent with the explicit teachings of this specification.

Materials and Methods

Cell cultures. All suspension cell lines were cultured in RPMI 1640 containing 10% heat-inactivated fetal calf serum (FCS). 10 mM HEPES (N-2-hydroxyethylpiperazine-n'-2-ethane sulfonic acid), 2 mM L-glutamine, 50 µg/ml gentamicin and $5 \times 10^{-5}$M 2-mercaptoethanol. IL-2-dependent cells were supplemented with 100 U/ml of recombinant human IL-2 (Cetus Corporation, Emeryville, Calif.). The suspension cells were passaged at a cell concentration of $0.5-4 \times 10^6$ cells/ml and recultured in fresh culture media twice a week. All monolayer cells were passaged twice a week at an initial cell concentration of $2 \times 10^6$ cells/ml. The tissue culture fluids (TCF) from FIV-infected cells were harvested twice a week, spun at 3000 rpm for 1 hour to remove residual cells, and stored at −20° C., or at −70° C. for those TCF scheduled to be used immediately upon testing. FIV-susceptible cells ($1 \times 10^6$ cells/ml) were infected with FIV having a reverse transcriptase (RT) activity of about 30,000 cpm/ml.

FIV purification. Tissue culture fluids from FIV-infected cell lines were individually centrifuged at 2000 to 3000 rpm for 1 hr to remove cells. Virus in the TCF was pelleted by ultracentrifugation at 16,000 rpm for 2 hours, and purified by ultracentrifugation first on a 10/50% (w/v) discontinuous sucrose gradient and then on a 10/50% continuous sucrose gradient (Pederson et al., 1987; Yamamoto et al., 1988). Each of the viral isolates was inactivated with 1.25% sterile paraformaldehyde (0.22 µm sterile filtered) for 18 hr and subsequently extensively dialyzed against sterile PBS. The inactivated viruses were diluted to a concentration of 500 µg/ml with sterile PBS and 250 µg/0.5 ml of each strain was placed in sterile microfuge tube and stored at −70° C. The inactivated FIV strains were thawed at room temperature and 250 µg of inactivated virus in 0.5 ml sterile PBS was combined with 0.5 ml of adjuvant just prior to immunization. FIV-infected cell lines were separately inactivated with 1.25% sterile paraformaldehyde for 18 hr, washed 3 times with sterile PBS, resuspended in fresh sterile PBS at concentration of about $5.0 \times 10^7$ cells/ml in sterile tubes and stored at 4° C. Typically, about $2.5 \times 10^7$ inactivated infected cells in 0.5 ml sterile PBS were combined with 0.5 ml of adjuvant just prior to immunization. 250 µg/0.5 ml of adjuvant just prior to immunization. 250 µg/0.5 ml of adjuvant just prior to immunization. 250 µg/0.5 ml of threonyl muramyl dipeptide (MDP MF75.2 adjuvant; Chiron Corporation, Emeryville, Calif.) was used as an adjuvant.

CTL assay. Peripheral blood mononuclear cells (PBMC) were stimulated with Concanavalin A (Con A) for 3 days prior to infection with FIV for 10 days (Song et al., 1992). These cells served as target cells for the CTL assay. CTL activity was generated by co-culturing Con A-stimulated PBMC with autologous UV- and radiation inactivated FIV-infected PBMC for 5 days. These cells served as the stimulated effector cells. On the assay day, target cells were labeled with 50 µCi of $Na^{51}CrO_4$ for 1 to 3 hours, washed 3 times, and then a fixed number of labeled target cells ($5 \times 10^4$ cells/well) were added to microtiter plates. Effector cells were added in triplicate at various effector/target cell ratios (i.e., 100:1, 50:1, and 10:1). Plates were centrifuged for 1 minute at 400 rpm and incubated at 37° C. for 4 hours. Control $^{51}$Cr-labeled target cells were lysed with detergent to obtain maximal release values. Supernatants from the test sample wells were collected and radiation was quantified using a gamma counter. Spontaneous release was determined by incubating $^{51}$Cr-labeled target cells in the absence of effector cells. Percentage of specific cytotoxicity was calculated as:

$$\% \text{ cytotoxicity} = (100) \frac{(\text{mean cpm test release} - \text{mean cpm spontaneous release})}{(\text{mean cpm maximum release} - \text{mean cpm spontaneous release})}$$

Immunoblot and enzyme linked immunosorbent assays (ELISA). Sucrose gradient purified virus was used as substrate for an immunoblot assay as described in Yamamoto et al., 1993. $FIV_{Pet}$ from tissue culture fluid of infected cells was clarified by low speed centrifugation (2000 rpm for 45 min), concentrated by ultracentrifugation (16,000 rpm for 2 hr), and purified by ultracentrifugation on a 10/50% (w/v) continuous sucrose gradient. The virus purified by this procedure was used as the substrate for the immunoblot assay.

A modification of an immunoblot technique previously described was used (Yamamoto et al., 1991 a). Virus blot strips were prepared by solubilizing virus in 0.1% SDS, followed by electrophoresis on 10% SDS-polyacrylamide gel and electrophoretic transfer onto nitrocellulose membrane. Serum samples from vaccinated cats were diluted to 1:50 in Buffer 3 (0.15 M sodium chloride, 0.001 M editic acid, 0.05 M TRIS base, 0.05% Tween 20, and 0.1% bovine serum albumin) and incubated with virus blot strips in separate wells of immunoblot plate for 18 hrs at 37° C. The blot strips were washed individually with wash solution (0.15 M NaCl and 0.05% Tween 20 in deionized $H_2O$), incubated with biotinylated anti-cat IgG (Vector Laboratories, Burlingame, Calif.) for 1 hr at 37° C., and washed three times with wash solution. The strips were then incubated individually with horseradish peroxidase conjugated Streptavidin (Vector Laboratories) for 30 min. After extensive washing, each strip was incubated with a fresh substrate solution (0.05% diaminobenzidine, 400 µg/ml $NiCl_2$, and 0.01% $H_2O_2$ in 0.1 M Tris buffer, pH 7.4) at room temperature. The reaction was stopped with excess distilled $H_2O$ upon establishment of visible bands, and the strips were blot dried. The molecular weights of the bands on the immunoblots were then determined by comparing them with the migration distance of the molecular weights standards on a strip previously stained with amido black. Positive and negative control serum were included in each immunoblot analysis as internal controls for diagnostic evaluation.

The viral antigen-specific ELISA has been previously described (Yamamoto et al., 1991a; Yamamoto et al., 1993).

Sucrose gradient purified $FIV_{Pet}$ and surface envelope (SU) and transmembrane (TM) peptides of both conserved (C) and variable (V) regions of $FIV_{Pet}$ were coated on 96 well Immunolon plates (Dynatech Laboratories, Inc., Chantilly, Va.) at 250 ng/well with bicarbonate buffer (pH 9.6) for 12 to 18 hours at 37° C. and were used as substrates for ELISA. The amino acid sequence of the SU-V3-2 peptide is: Gly Ser Trp Phe Arg Ala Ile Ser Ser Trp Lys Gin Arg Asn Arg Trp Glu Trp Arg Pro Asp Phe (SEQ ID NO. 1); and the amino acid sequence of the TM-C1 peptide is: Gin Glu Leu Gly Cys Asn Gln Asn Gln Phe Phe Cys Lys Ile (SEQ ID NO. 2). The synthetic peptides were synthesized on a Biosearch 9500 peptide synthesizer (Biosearch, San Rafael, Calif.) using FMOC peptide synthesis chemistry (Magazine et al., 1988). Purity of the synthesized peptides was determined by the presence of a single peak on a reversed-phase high-performance liquid chromatography and confirmed by amino acid sequence analysis performed on the peak sample.

(0.005% tetramethylbenzidine and 0.015% $H_2O_2$ in 0.96-% citrate solution) at room temperature. The reaction was stopped with 0.1 M hydrofluoric acid upon establishment of visible reaction color in the sequentially diluted standards consisting of known FIV-positive cat serum. Light absorption was measured with a BioRad ELISA reader (Bio-Rad Laboratories, Hercules, Calif.) at optical density of 414 nm.

Polymerase Chain Reaction (PCR). The proviral DNA levels of infected cells were monitored by differential PCR, which was recently developed to distinguish multiple FIV strains from the same or different subtypes (Okada et al., 1994). As a means of increasing the sensitivity of PCR, the nested PCR primer sets shown in Table 1 were used. PCR was performed in a two stage reaction, first with a pair of outer primers (common for all FIV strains) under conditions as described in Okada et al., 1994. In the second PCR stage, $\frac{1}{25}$ of the first stage product was amplified using the inner primers (specific for each FIV strain). Using nested PCR, cells infected with $FIV_{Pet}$, $FIV_{UK8}$, $FIV_{Bang}$, $FIV_{Aom1}$, $FIV_{Aom2}$ and $FIV_{Shi}$ can be distinguished from each other.

TABLE 1

Primer sets for differential PCR.

| Subtype | Strain | Primer (orientation) | Sequence | Position* |
|---|---|---|---|---|
| Outer Primer Sets | | | | |
| All | NA | common (+) | GAAATGTATAATATTGCTGG (SEQ ID NO. 3) | 1570-1589 |
| | | common (−) | GAATTGATTTTGATTACATCC (SEQ ID NO. 4) | 2112-2092 |
| Inner Primer Sets | | | | |
| A | Petaluma | Pet (+) | TAGTAGTTATAGTGGTACTA (SEQ ID NO. 5) | 1659-1678 |
| | | Pet (−) | TCTTTAAGGCTTCAGTCACCT (SEQ ID NO. 6) | 1984-1964 |
| | UK-8 | UK8 (+) | GTACAAATAGTAGTAGTACAA (SEQ ID NO. 7) | 1646-1666 |
| | | UK8 (−) | TCTTTAAGGCTTCAGTCACCT (SEQ ID NO. 8) | 1984-1964 |
| B | Bangston | Bang (+) | GGGACTACTAGCAATGGAATA (SEQ ID NO. 9) | 1654-1674 |
| | | Bang (−) | AGTGCCTCAGTTATTTTATCC (SEQ ID NO. 10) | 1979-1959 |
| | Aomori-1 | Ao1 (+) | TGGGACTGATGATAGTAAAAC (SEQ ID NO. 11) | 1654-1674 |
| | | Ao1 (−) | AGTGCCTCAGTTATTTTATCC (SEQ ID NO. 12) | 1979-1959 |
| | Aomori-2 | Ao2 (+) | TGGGACTGATAATAGTGAAAC (SEQ ID NO. 13) | 1654-1674 |
| | | Ao2 (−) | AGTGCCTCAGTTATTTTATCC (SEQ ID NO. 14) | 1979-1959 |
| D | Shizuoka | Shi (+) | TCATCATTTCCAACATGTC (SEQ ID NO. 15) | 1663-1681 |
| | | Shi (−) | AATGCTTCAGTTATTTGATC (SEQ ID NO. 16) | 1979-1960 |

*Nucleotide positions correspond to those of Petaluma sequence and the numbers represent the position from the start of env sequence.

The peptide coated plates were washed once with Buffer 3 immediately prior to use. The serum samples were diluted at 1:200 in Buffer 3 and incubated in the FIV antigen coated wells for 1 hr at 37° C., then washed 6 times. The wells were washed with wash solution, incubated with biotinylated anti-cat IgG (Vector Laboratories, Burlingame, Calif.) for 1 hr at 37° C., washed 6-times, and incubated with horseradish peroxidase conjugated Streptavidin (Vector Laboratories) for 1 hr at 37° C. The wells were then washed 6 times with wash solution and incubated with ELISA substrate solution The approximate amount of proviral DNA per cell was determined by semi-quantitative PCR, in which varying dilutions of DNA extracted from a known number of cells are made. For example, if $10^5$ cells are used for DNA extraction, then a $10^{-5}$ dilution of the DNA preparation will approximately correspond to the DNA present in a single cell. PCR was performed on these varying DNA dilutions and the final dilution that gave a positive PCR result is considered the end-point dilution. The number of cells corresponding to the end-point dilution is used to determine the percentage of cells infected with virus in a given cell preparation according to the following formula:

$$\% \text{ infected cells} = \frac{1}{Z} \times 100$$

where Z=the number of cells corresponding to the end-point dilution.

Reverse transcriptase (RT) assay. The presence of RNA-dependent DNA polymerase (RT) was assayed in cell culture supernatants essentially as described by Rey et al. The RT assay for detecting FIV used poly(rA)-oligo($dT_{12-18}$) as an exogenous template primer, four different deoxyribonucleotide triphosphates, 20 mM KCl with $Mg^{++}$ as divalent cation and 5 μCi [$^3$H]-labeled thymidine triphosphate (TTP) per sample. Five μCi [$^3$H]TTP gave an average total count of 1,200,000 cpm using scintillation fluid mixture (1 part xylene to 9 part Research Products International biodegradable counting scintillant) on a Beckman LS250 scintillation counter (Beckman Instruments, Inc., Palo Alto, Calif.). As a result, RT values for samples tested will be below 1,200,000 cpm/ml.

Viral neutralization assay. A strategy for developing strain- and subtype-specific VN assays has been described (Okada et al., 1994). Serial dilutions of heat-inactivated sera were incubated with 100 $TCID_{50}$ of each FIV strain for 45 minutes at 37° C. in a 24-well plate prior to addition of feline peripheral blood mononuclear cells (PBMC) ($4 \times 10^5$ cells/ml) or FIV-susceptible FeT-1C cells ($2 \times 10^5$ cells/ml). After 3 days of culturing, the cells were washed once with Hank's balanced salt solution to remove residual virus from the culture and then the cells were resuspended in fresh culture media (RPMI-1640 containing 10% heat-inactivated fetal calf serum, 10 mM HEPES buffer, 50 μg/ml gentamicin, $5 \times 10^{-5}$ M 2-mercaptoethanol, and 100 Units/ml human recombinant IL-2). Virus infection of cells was monitored by $Mg^{++}$-dependent RT assays of the culture fluids harvested on 9, 12, 15, and 18 days of culture. Sera were considered positive for VN antibodies when RT activity was ≦25% of infected control cultures consisting of SPF serum.

Following are examples which illustrate procedures, including the best mode, for practicing the invention. These examples should not be construed as limiting. All percentages are by weight and all solvent mixture proportions are by volume unless otherwise noted.

EXAMPLE 1

FIV-infected Cell Lines

A novel interleukin-2 (IL-2) dependent feline T-cell line, designated as FeT-1C, which is a mother line of an IL-2-dependent FeT-1M clone, was used to establish individual cell lines chronically infected with either $FIV_{Pet}$, $FIV_{Dix}$, $FIV_{UK8}$, $FIV_{Bang}$, $FIV_{Aom2}$, or $FIV_{Shi}$. The FeT-1M clone (also referred to as FIV-Fet1M) has been described in U.S. Pat. No. 5,275,813, which is herein incorporated by reference, and was used to produce an 1L-2-independent cell line, FL-4 (also described in U.S. Pat. No. 5,275,813), that chronically produces $FIV_{Pet}$. The FeT-1C cell line is highly infectable with different isolates from FIV subtypes A, B, and D. Long-term passaging of the FeT-1C cell line decreases its infectability, especially to FIV subtype D; therefore, the passage number should be less than about 35 passages for optimal FIV infection rates or for its use in VN assays. Semi-quantitative PCR and viral core antigen analyses indicated that all the cell lines exposed to FIV were significantly infected with individual FIV strains.

An IL-2 independent feline cell line susceptible to FIV infection has also been developed from FeT-1C cells. This cell line, designated as FeT-J, can be infected with FIV by co-culture using FIV infected media or cells. For example, an $FIV_{Bang}$-infected FeT-1C cell line was co-cultured in the absence of IL-2 with uninfected FeT-J cells to establish an IL-2-independent $FIV_{Bang}$-infected FeT-J cell line (designated as Bang/FeT-J). In the co-culture method of infection, Bang/FeT-1C cells were combined with uninfected FeT-J cells at a ratio of from about 2:1 to about 10:1 (infected: uninfected). The cell mix was cultured in media in the absence of IL-2 for several days and the FeT-1C cells were allowed to die off. The remaining cells consisted of $FIV_{Bang}$-infected FeT-J cells. Thus, FIV-infected FeT-1C cells can be used to infect FeT-J cells and establish IL-2-independent FeT-J cell lines infected with different FIV subtypes. The co-cultivation method with FIV infected FeT-1C cells resulted in IL-2-independent FeT-J cell lines producing moderate to high levels of different FIV subtypes.

The FeT-1C cell line was also infected with $FIV_{Shi}$ and extensively passaged to produce an IL-2-dependent cell line designated as Shi/FeT-1C. The Shi/FeT-1C cell line was later co-cultured with FeT-J in the absence of 1L-2 and the resulting 1L-2-independent $FIV_{Shi}$-infected cell line was designated as Shi/FeT-J. The IL-2-independent Shi/FeT-J cell line produces higher levels of $FIV_{Shi}$ than IL-2-dependent Shi/FeT-1C cell line (FIG. 1).

The development of a FeT-J cell line infected with $FIV_{Bang}$ was also performed without the use of the FeT-1C cell line. The FeT-J cell line was directly infected with cell-free $FIV_{Bang}$ inoculum and extensively passaged without IL-2. The resulting IL-2-independent $FIV_{Bang}$ producer cell line was designated Bang/FeT-J. The Bang/FeT-J cell line produced higher levels of $FIV_{Bang}$ than the IL-2-dependent Bang/FeT-1C cell line which was developed by infecting FeT-1C cell line with $FIV_{Bang}$ (FIG. 1).

EXAMPLE 2

Multi-subtype FIV Vaccines

FIV-infected cells were removed from supernatants by centrifugation, inactivated, and used as vaccine. Similarly, whole FIV virus were pelleted from infected cell-free supernatant by ultracentrifugation and inactivated. Both infected cells and virus were inactivated by treatment with 1.25% paraformaldehyde for 24 hours at 5° C., followed by extensive washing or dialysis against PBS, respectively. This method efficiently inactivates FIV without loss of immunogenicity. FIV immunogens produced according to the subject method are highly effective for inducing protective immunity (Yamamoto et al., 1993; Yamamoto et al., 1991a; Yamamoto et al., 1991b). It is contemplated that attenuated viral isolates could also be used in the vaccine compositions of the subject invention.

Although an $FIV_{Shi}$-infected FeT-1C cell line was super-infected with the $FIV_{Pet}$ strain to produce a single cell line infected with multiple subtypes of FIV (i.e., a multi-subtype A/D FeT-1C cell line), within two months of co-infection the $FIV_{Shi}$ proviral levels decreased from 50% to less than 5% whereas $FIV_{Pet}$ proviral levels concomitantly increased to about 50%. Thus, the maintenance of a single cell line infected with multiple subtypes of FIV for use as an FIV vaccine is not the preferred embodiment of the subject invention.

Figure 2:
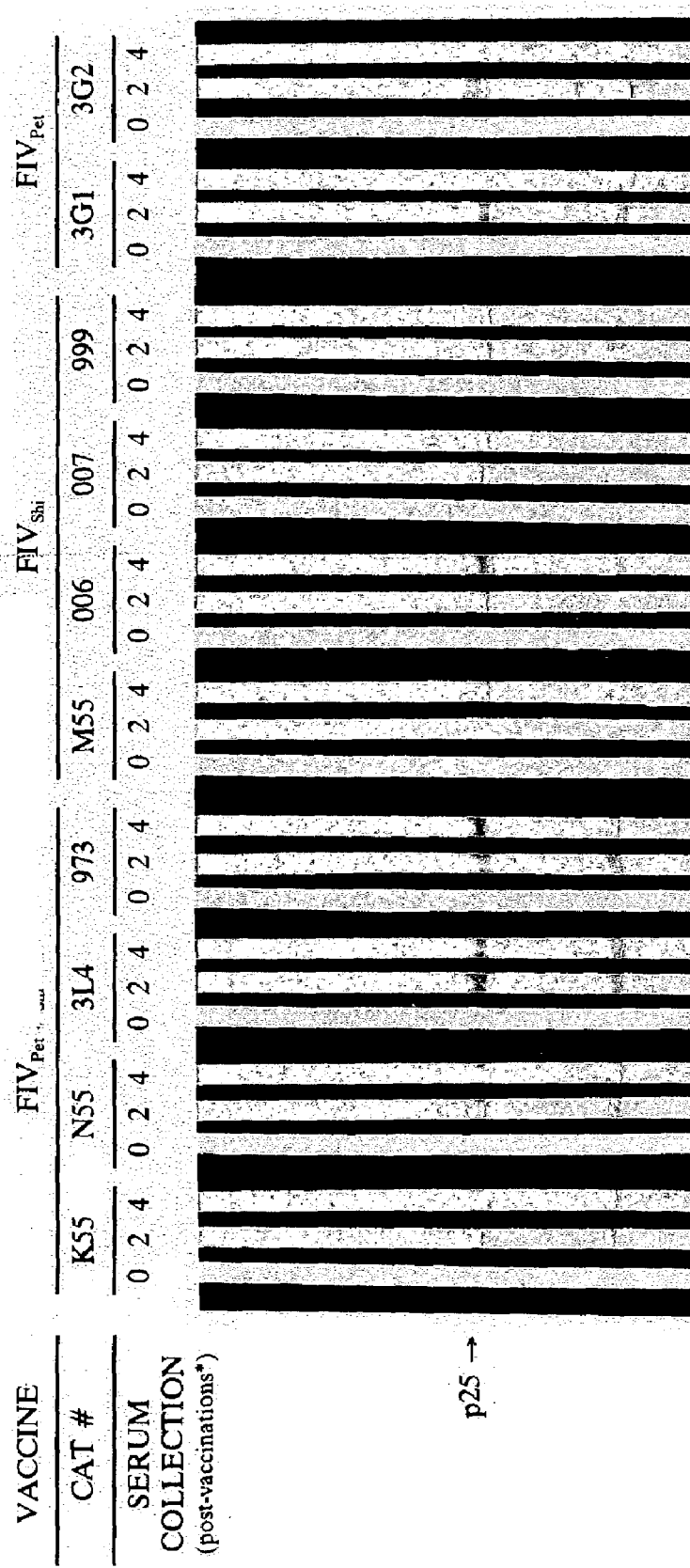

Consequently, in one embodiment of the subject invention, vaccine compositions were developed from two individual cell lines, each line being infected with a different FIV subtype. In a specific embodiment, the dual-subtype FIV vaccine composition comprised a combination of an FIV subtype A-infected cell line (Pet/FL-4) with an FIV subtype D-infected cell line (Shi/FeT-1C). The A-subtype and D-subtype infected cell lines were inactivated as described, combined in equal cell numbers ($2.5 \times 10^7$ cells each in 250 µg of MDP) and used to immunize cats. Three SPF cats were vaccinated with inactivated Pet/FL-4 cells and four other cats were vaccinated with inactivated Shi/FeT-1C cells ($2.5 \times 10^7$ cells/dose). After a series of four vaccinations, the dual-subtype (Pet/FL-4 and Shi/FeT-1C) vaccine induced anti-FIV antibodies, including significant VN antibody titers, to both FIV strains tested (FIG. 2 and Table 2, Trial I). Four dual-subtype (Pet/FL-4 and Shi/FeT-1C) vaccinated cats were challenged with $FIV_{Bang}$ (50 $CID_{50}$). All three Pet/FL-4 vaccinated and two of the Shi/FeT-1C vaccinated cats were challenged with 50 $CID_{50}$ of $FIV_{Bang}$. The two remaining Shi/FeT-1C vaccinated cats were challenged with 50 $CID_{50}$ of $FIV_{Shi}$.

All dual-subtype vaccinated cats were negative for $FIV_{Bang}$ by virus isolation and PCR of PBMC at 6 weeks post-infection (pi), whereas all sham immunized cats were positive for either $FIV_{Bang}$ or $FIV_{Shi}$ by virus isolation and PCR at 6 weeks post-infection (Table 2, trial I). In contrast, one cat each from Pet/FL-4 vaccinated and Shi/FeT-1C vaccinated groups which was challenged with $FIV_{Bang}$ was positive for $FIV_{Bang}$. As expected, all cats vaccinated with $FIV_{Shi}$ and subsequently challenged with $FIV_{Shi}$ were negative for $FIV_{Shi}$ at 6 weeks post-infection. Thus, the dual-subtype vaccine specifically exemplified prevented or delayed infection against homologous $FIV_{Shi}$ challenge as well as against heterologous $FIV_{Bang}$ challenge.

The dual-subtype vaccinated cats (Pet/FL-4 cells and Shi/FeT-1C cells) developed FIV antibodies specific for the viral core protein p25 (also call FIV p28) after the second immunization (FIG. 2). Higher antibody titers to other viral antigens were demonstrated after the third to fourth immunization. VN antibodies to $FIV_{Pet}$ developed after the second immunization, whereas VN antibodies to $FIV_{Shi}$ developed after the fourth immunization (Table 4). CTL responses to $FIV_{Pet}$ and $FIV_{Shi}$ were detected as early as the third immunization in all cats tested (Table 3) and stronger CTL responses to both strains were developed after the fourth immunization. Further, two of the three cats tested developed CTL responses to $FIV_{Bang}$ after the fourth immunization. Results indicate that after 4 vaccinations, the dual-subtype vaccine induced strong CTL responses to $FIV_{Pet}$ and $FIV_{Shi}$ (Table 3) and high FIV antibodies, including VN antibody titers, to both FIV strains (Table 4).

The cats immunized with inactivated Shi/FeT-1C cells developed FIV antibodies specific for the viral core protein p25 after the second immunization and antibodies to other viral antigens after the third immunization (FIG. 2). VN antibodies to $FIV_{Shi}$ in these cats developed after the fourth immunization, whereas VN antibodies to $FIV_{Pet}$ were not detected over the course of the immunizations. Both of the Shi/FeT-1C vaccinated cats developed CTL responses to $FIV_{Shi}$ only after the fourth immunization but did not develop CTL responses to $FIV_{Pet}$, even after the fourth immunization (Table 3).

Cats immunized with inactivated Pet/FL-4 cells developed antibodies to p25 after the second immunization (FIG. 2) and to other viral antigens, including VN antibodies to $FIV_{Pet}$, after the second to third immunization (Table 4). The only CTL responses detected in cats immunized with Pet/FL-4 cells were to $FIV_{Pet}$. Overall, the dual subtype FIV vaccine induced more rapid and higher VN antibody titers and CTL responses to both FIV strains than the single-subtype vaccine. Sham immunized SPF cats did not develop viral antibodies, VN antibodies, or anti-FIV CTL responses.

TABLE 2

Protection of cats with multi-subtype FIV vaccine

| Vaccine type | No. of Cats | FIV challenge strain ($CID_{50}$)[1] | Average VN Antibodies at Day 0 pi against[2] | | | Virus Isolation & PCR | Protection Rate (%) |
| --- | --- | --- | --- | --- | --- | --- | --- |
| | | | Pet | Shi | Bang | | |
| Dual-subtype Vaccine Trial I (A + D): | | | | | | | |
| Pet/FL-4 cell + Shi/FeT-1C cell | 5 | $FIV_{Bang}$(50 $CID_{50}$) | 1000 | 550 | <10 | 3/5 Negative | 3/5 (60% at 6 wk pi) |
| Pet/FL-4 cell | 3 | $FIV_{Bang}$(50 $CID_{50}$) | 1000 | <10 | <10 | All Positive | 0/3 (0% at 6 wk pi) |
| Shi/FeT-1C cell | 2 | $FIV_{Bang}$(50 $CID_{50}$) | <10 | 75 | <10 | All Positive | 0/2 (0% at 6 wk pi) |
| Shi/FeT-1C cell | 2 | $FIV_{Shi}$(50 $CID_{50}$) | <10 | 30 | <10 | All Positive | 0/2 (0% at 6 wk pi) |
| sham | 3 | $FIV_{Bang}$(50 $CID_{50}$) | <10 | <10 | <10 | All Positive | 0/3 (0% at 6 wk pi) |
| sham | 2 | $FIV_{Shi}$(50 $CID_{50}$) | <10 | <10 | <10 | All Positive | 0/2 (0% at 6 wk pi) |
| Triple-subtype Vaccine Trial II (A + B + D):[4] | | | | | | | |
| Pet/FL-4 cell + Bang/FeT-J cell + Shi/FeT-1C cell[5] | 3 | $FIV_{UK8}$ | 1000 | 370 | 1000 | NA | 2/3 (67% at 24 wk pi) |
| Bang/FeT-J cell | 2 | $FIV_{UK8}$ | <10 | <10 | 1000 | NA | 0/2 |
| Bang/FeT-J cell | 2 | $FIV_{Bang}$ | <10 | <10 | 100 | NA | 1/2 |
| Sham Uninfected FeT-J | 2 | $FIV_{UK8}$ | <10 | <10 | <10 | NA | |
| Uninfected FeT-J | 2 | $FIV_{UK8}$ | <10 | <10 | <10 | NA | 0/2 |
| Sham Adjuvant only | 1 | $FIV_{UK8}$ | <10 | <10 | <10 | NA | 0/2 |

TABLE 2-continued

Protection of cats with multi-subtype FIV vaccine

| Vaccine type | No. of Cats | FIV challenge strain $(CID_{50})^1$ | Average VN Antibodies at Day 0 pi against[2] | | | Virus Isolation & PCR | Protection Rate (%) |
| --- | --- | --- | --- | --- | --- | --- | --- |
| | | | Pet | Shi | Bang | | |
| Uninfected FeT-J | 1 | $FIV_{Bang}$ | <10 | <10 | <10 | NA | 0/1 |
| Sham Adjuvant only | 2 | $FIV_{Bang}$ | <10 | <10 | <10 | NA | 1/2 |

[1] All FIV challenge inocula were produced in vitro by infecting primary PBMC from SPF cats. All aliquoted inocula were stored in −70° C. and thawed at room temperature just prior to use.
[2] pi = post FIV infection.
[3] ND = not done.
[4] VN results are after third vaccination.
[5] Fourth vaccination will be performed with inactivated Shi/FeT-J cells instead of inactivated Shi/FeT-lC cells.

TABLE 3

CTL responses from dual-subtype vaccinated cats.

CHROMIUM RELEASE (% LYSIS)

| Cat# | Vaccine Type | CTL Target | 3rd Vaccination Effector:Target Ratio | | | 4th Vaccination Effector:Target Ratio | | |
| --- | --- | --- | --- | --- | --- | --- | --- | --- |
| | | | 10:1 | 50:1 | 100:1 | 10:1 | 50:1 | 100:1 |
| K55 | Pet + Shi | Pet | 0 | 9 | 20 | 17 | 25 | 33 |
| | | Bang | ND | ND | ND | 0 | 0 | 14 |
| | | Shi | 0 | 9 | 8 | 7 | 11 | 17 |
| 3L4 | Pet + Shi | Pet | 0 | 11 | 19 | 0 | 11 | 19 |
| | | Bang | ND | ND | ND | 0 | 0 | 0 |
| | | Shi | 0 | 9 | 13 | 0 | 9 | 17 |
| N55 | Pet + Shi | Pet | ND | ND | ND | 0 | 11 | 17 |
| | | Bang | ND | ND | ND | 0 | 0 | 7 |
| | | Shi | ND | ND | ND | 0 | 9 | 15 |
| M55 | Shi | Pet | 0 | 0 | 0 | 0 | 0 | 0 |
| | | Bang | ND | ND | ND | 0 | 0 | 0 |
| | | Shi | 0 | 0 | 0 | 0 | 7 | 15 |
| 007 | Shi | Pet | 0 | 0 | 0 | 0 | 0 | 0 |
| | | Bang | ND | ND | ND | 0 | 0 | 0 |
| | | Shi | 0 | 0 | 0 | 0 | 0 | 8 |
| 2H5D | Pet | Pet | 0 | 7 | 15 | 6 | 15 | 25 |
| | | Bang | ND | ND | ND | 0 | 0 | 0 |
| | | Shi | 0 | 0 | 0 | 0 | 0 | 0 |
| 3G1 | Pet | Pet | 0 | 10 | 14 | 6 | 13 | 19 |
| | | Bang | ND | ND | ND | 0 | 0 | 0 |
| | | Shi | 0 | 0 | 0 | 0 | 0 | 0 |
| H7P | Sham | Pet | 0 | 0 | 0 | 0 | 0 | 0 |
| | | Bang | ND | ND | ND | 0 | 0 | 0 |
| | | Shi | 0 | 0 | 0 | 0 | 0 | 0 |

TABLE 4

Virus neutralization (VN) titers from dual-subtype vaccinated cats.

| Cat No. | FIV Vaccine | Pre-Vaccination | | | Post 2nd Vaccination | | | Post 4th Vaccination | | |
| --- | --- | --- | --- | --- | --- | --- | --- | --- | --- | --- |
| | | Pet | Bang | Shi | Pet | Bang | Shi | Pet | Bang | Shi |
| K55 | Pet + Shi | >10 | >10 | >10 | 100 | <10 | <10 | 1000 | <10 | 100 |
| 3L4 | Pet + Shi | >10 | >10 | >10 | 100 | <10 | <10 | 1000 | <10 | 1000 |
| N55 | Pet + Shi | >10 | >10 | >10 | 10 | <10 | <10 | 1000 | <10 | 1000 |
| 973 | Pet + Shi | >10 | >10 | >10 | 10 | <10 | <10 | 1000 | <10 | 100 |
| M55 | Shi | >10 | >10 | >10 | >10 | <10 | <10 | <10 | <10 | 50 |
| 006 | Shi | >10 | >10 | >10 | >10 | >10 | <10 | <10 | <10 | 100 |
| 007 | Shi | >10 | >10 | >10 | >10 | <10 | <10 | <10 | <10 | 10 |
| 999 | Shi | >10 | >10 | >10 | >10 | >10 | <10 | <10 | <10 | 50 |
| 3G1 | Pet | >10 | >10 | >10 | >10 | <10 | <10 | 1000 | <10 | <10 |
| 3G2 | Pet | >10 | >10 | >10 | 10 | <10 | <10 | 1000 | <10 | <10 |
| 2H5D | Pet | >10 | >10 | >10 | 100 | <10 | <10 | 1000 | <10 | <10 |
| 8C2 | Sham | >10 | >10 | >10 | >10 | >10 | >10 | >10 | >10 | >10 |
| 8C8 | Sham | >10 | >10 | >10 | >10 | >10 | >10 | >10 | >10 | >10 |
| H7P | Sham | >10 | >10 | >10 | >10 | >10 | >10 | >10 | >10 | >10 |

TABLE 4-continued

Virus neutralization (VN) titers from dual-subtype vaccinated cats.

| Cat No. | FIV Vaccine | Pre-Vaccination | | | Post 2nd Vaccination | | | Post 4th Vaccination | | |
|---|---|---|---|---|---|---|---|---|---|---|
| | | Pet | Bang | Shi | Pet | Bang | Shi | Pet | Bang | Shi |
| 8G8 | Sham | <10 | <10 | <10 | <10 | <10 | <10 | <10 | <10 | <10 |
| RF5 | Sham | <10 | <10 | <10 | <10 | <10 | <10 | <10 | <10 | <10 |

In a preferred embodiment, the vaccine composition of the subject invention comprises a triple-subtype FIV vaccine prepared from three cell lines, each cell line having been infected with a viral strain from a different FIV subtype (A or B or D). Three specific pathogen free cats were immunized with a triple-subtype ($FIV_{Pet}+FIV_{Bang}+FIV_{Shi}$) vaccine. Other cats were immunized with single-subtype $FIV_{Bang}$ vaccines to evaluate the immunogenicity of macrophage-tropic $FIV_{Bang}$ as a component of the vaccine. The VN antibody titer results indicate that both triple-subtype ($FIV_{Pet}+FIV_{Bang}+FIV_{Shi}$) and single-subtype $FIV_{Bang}$ vaccines elicited high antiviral antibody titers even after the second immunization (Table 2, trial II and Table 5). Thus, both lymphotropic and macrophage-tropic FIV can be used as components of the vaccine compositions of the present invention.

Figure 3:
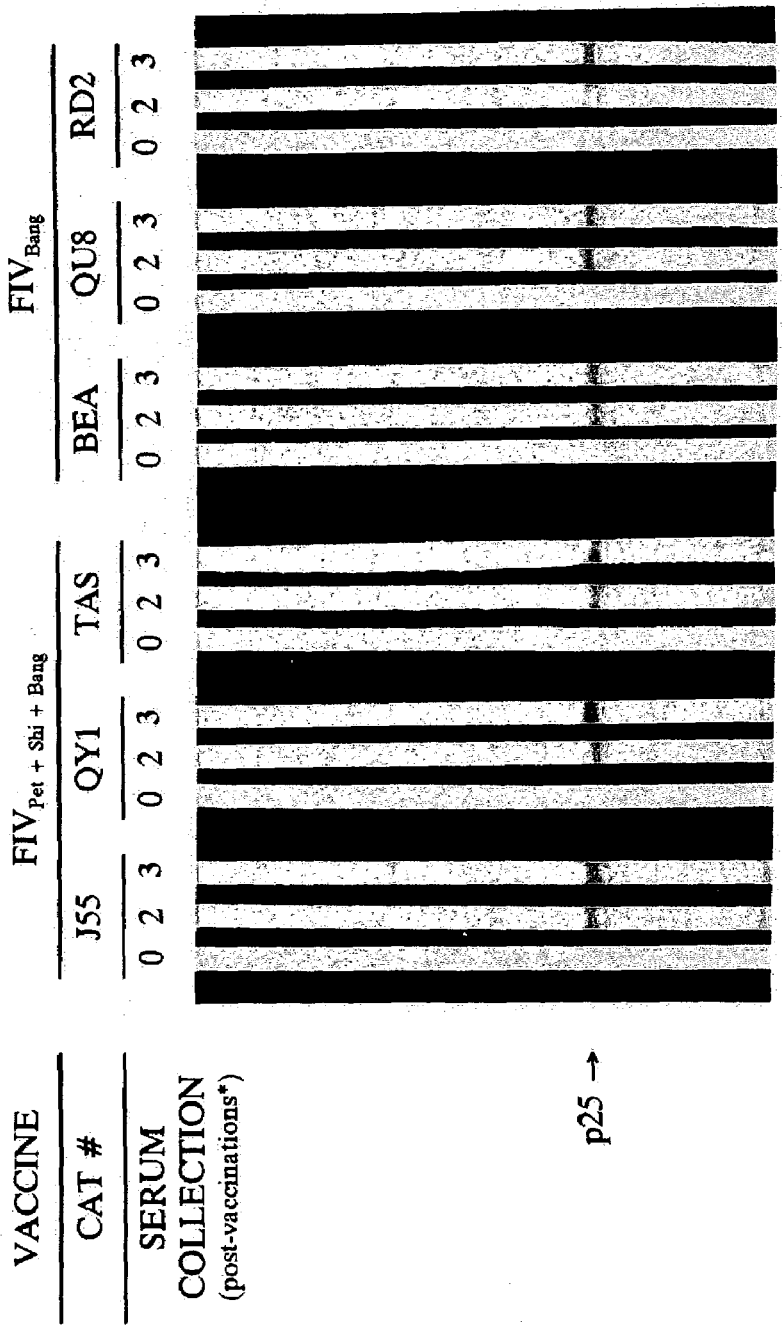
Figure 4A:
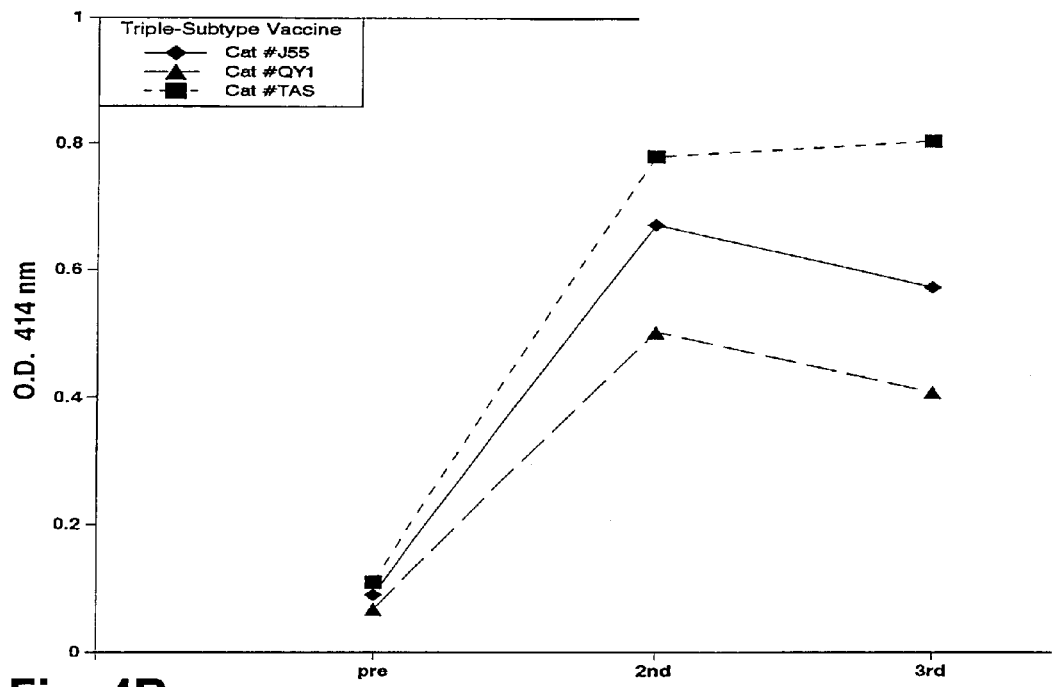
Figure 4B:
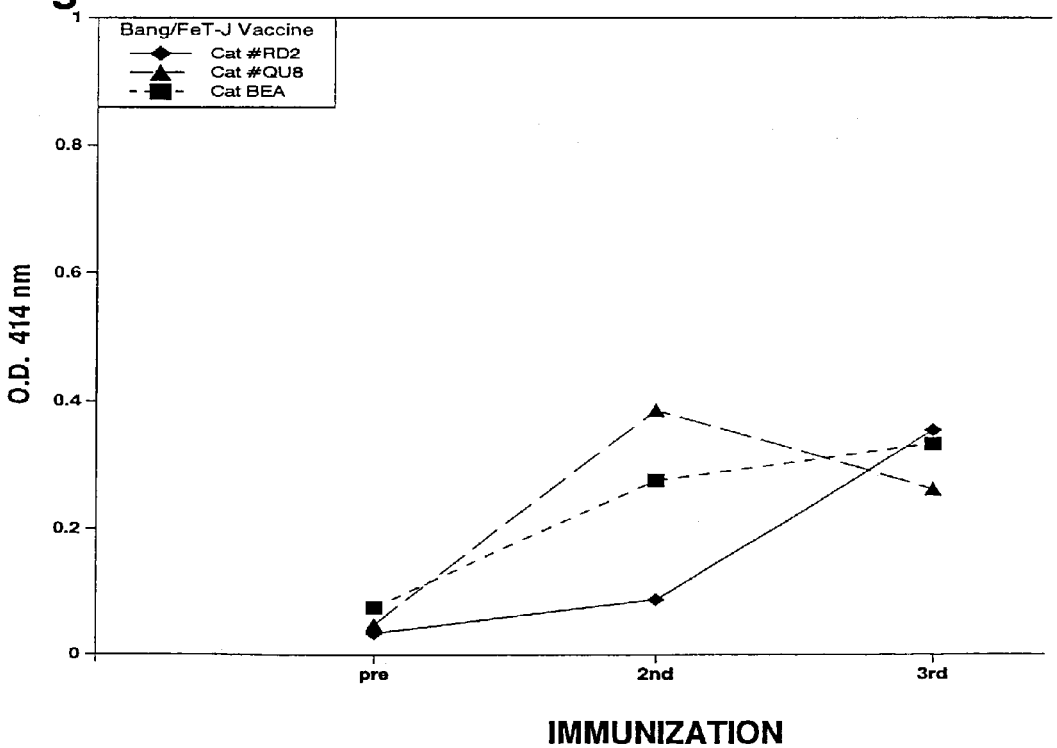
Figure 5A:
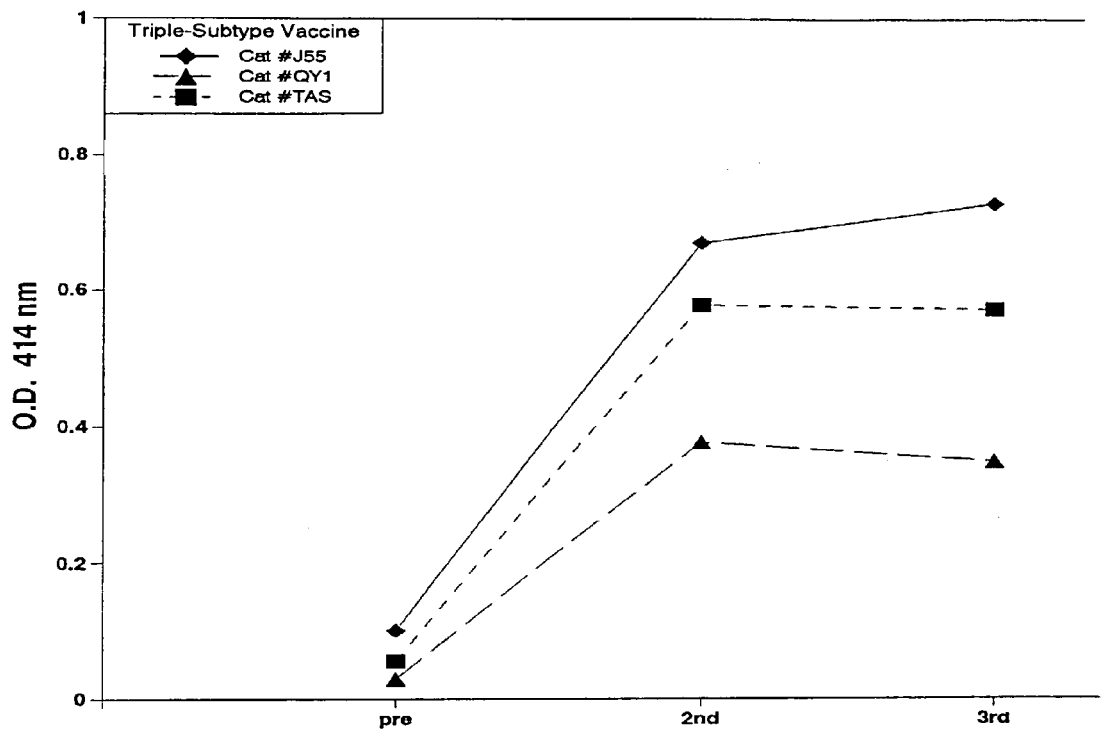
Figure 5B:
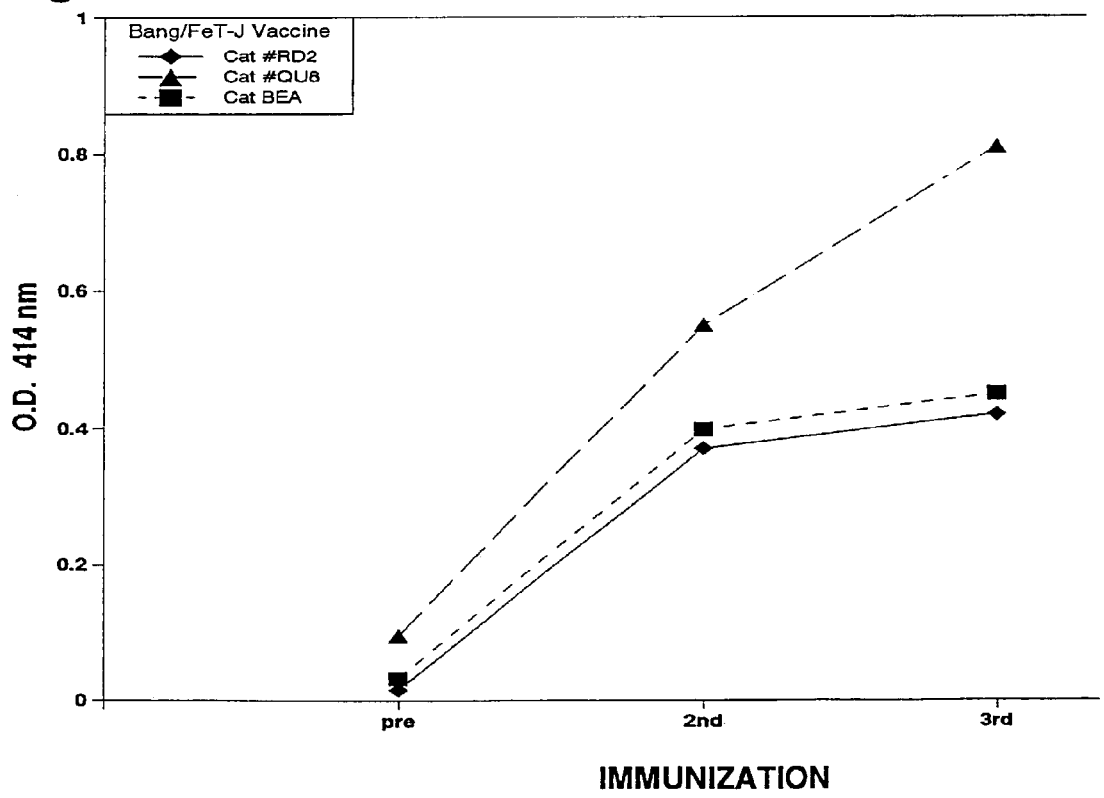

The three SPF cats immunized with a combination of inactivated Pet/FL-4, inactivated Bang/FeT-J, and inactivated Shi/FeT-1C cells ($2.5 \times 10^7$ cells each in 250 µg total of MDP) developed FIV antibodies specific for the viral core protein p25 and to other viral antigens, including FIV SU and TM envelope protein, after the second immunization (FIGS. 3, 4, 5). VN antibodies to $FIV_{Pet}$, $FIV_{Bang}$ and $FIV_{Shi}$ developed in the majority of cats soon after the second immunization and in all cats by the third immunization (Table 5). In addition, one cat had VN antibodies that cross reacted to $FIV_{UK8}$ after third immunization. Four SPF cats immunized only with inactivated Bang/FeT-J cells developed FIV antibodies specific for the viral core protein p25 and other viral antigens after the second immunization (FIG. 3). VN antibodies to $FIV_{Bang}$ in these cats developed after the second immunization (Table 5), whereas VN antibodies to $FIV_{Pet}$ and $FIV_{UK8}$ were not detected over the course of the immunizations. CTL responses of cats immunized three times with the triple-subtype FIV vaccine (Pet/FL-4, Bang/FeT-J and Shi/FeT-1C cells) to FIV A, B and D subtype target cells are shown in Table 6. CTL responses to all three FIV subtypes tested were detected. Thus, the triple-subtype vaccine induced a broad CTL response and more rapid and higher VN and SU-envelope antibody titers than the single-subtype vaccine. Neither uninfected FeT-J nor Sham immunized SPF cats developed viral antibodies or VN antibodies.

TABLE 5

Virus neutralization (VN) titers from triple-subtype vaccinated cats.

| CAT# | FIV VACCINE | Pre-Vaccination | | | | Post 2nd Vaccination | | | | Post 3rd Vaccination | | | |
|---|---|---|---|---|---|---|---|---|---|---|---|---|---|
| | | Pet | Bang | Shi | UK8 | Pet | Bang | Shi | UK8 | Pet | Bang | Shi | UK8 |
| J55 | Pet + Bang + Shi | <10 | <10 | <10 | <10 | 1000 | 1000 | <10 | <10 | 1000 | 1000 | 10 | <10 |
| QY1 | Pet + Bang + Shi | <10 | <10 | <10 | <10 | 100 | 1000 | 100 | <10 | 1000 | 1000 | 1000 | <10 |
| TAS | Pet + Bang + Shi | <10 | <10 | <10 | <10 | <10 | 1000 | 10 | <10 | 100 | 1000 | 100 | 100 |
| BEA | Bang | <10 | <10 | <10 | <10 | <10 | 100 | <10 | <10 | <10 | 1000 | <10 | <10 |
| QU8 | Bang | <10 | <10 | <10 | <10 | <10 | 10 | <10 | <10 | <10 | 100 | <10 | <10 |
| RD2 | Bang | <10 | <10 | <10 | <10 | <10 | 100 | <10 | <10 | <10 | 100 | <10 | <10 |
| 3G4 | Uninfected FeT-J | <10 | <10 | <10 | <10 | <10 | <10 | <10 | <10 | <10 | <10 | <10 | <10 |
| 3G5 | Uninfected FeT-J | <10 | <10 | <10 | <10 | <10 | <10 | <10 | <10 | <10 | <10 | <10 | <10 |
| 3G6 | Sham | <10 | <10 | <10 | <10 | <10 | <10 | <10 | <10 | <10 | <10 | <10 | <10 |
| 3G7 | Sham | <10 | <10 | <10 | <10 | <10 | <10 | <10 | <10 | <10 | <10 | <10 | <10 |

The VN titers are the average titers of two separate VN assays.

TABLE 6

CTL responses of triple-subtype vaccinated cats after 3rd immunization

| Cat No. | Target FIV | E:T Ratio | CTL Activity (% chromium release) |
|---|---|---|---|
| QY1 | $FIV_{Pet}$ | 100 | 44% |
| | | 50 | 21% |
| | | 10 | 4% |
| QY1 | $FIV_{Bang}$ | 100 | 13% |
| | | 50 | 6% |
| | | 10 | 1% |
| QY1 | $FIV_{UK8}$ | 100 | 23% |
| | | 50 | 8% |
| | | 10 | 2% |
| Tas | $FIV_{Bang}$ | 100 | 8% |
| | | 50 | 3% |
| | | 10 | 1% |
| Tas | $FIV_{Shi}$ | 100 | 3% |
| | | 50 | 1% |
| | | 10 | 0.3% |
| J55 | $FIV_{UK8}$ | 100 | 10% |
| | | 50 | 2% |
| | | 10 | 1% |

EXAMPLE 3

VN Antibodies to FIV Subtypes

An assay for VN antibodies to FIV was also developed using the FeT-1C cells of the subject invention. Serum from FIV$_{Pet}$-infected cats and SPF cats vaccinated with inactivated Pet/FL-4 cells or inactivated FIV$_{Pet}$ virus were tested for VN antibody titer using either FeT-1C cells or PBMC according to the VN assay method described herein. Sera from two SPF cats which were unvaccinated and FIV uninfected were used as control sera. Sera from vaccinated and FIV infected cats had a high VN antibody titer of 1000 or greater, whereas sera from unvaccinated SPF cats had no detectable N antibody titer. The FeT-1C-based VN assay gives VN antibody titer results comparable to those obtained using primary PBMC from cats (Table 6). This finding demonstrates that VN antibody titers in a VN assay using FeT-1C cells correlates with those results obtained with a VN assay using PBMC. Therefore, FeT-1C cells can be advantageously used in place of PBMC in the standard VN assay for FIV since FeT-1C cells can be infected with all the FIV subtypes and can be readily propagated in tissue culture.

TABLE 7

VN titers assayed on FeT-1C and PBMC

| Serum source | VN titers | |
|---|---|---|
| | FeT-1C | PBMC |
| Vaccinated[1] | 5000 | 5000 |
| Vaccinated[1] | >1000 | >1000 |
| Infected[2] | 1000 | 1000 |
| Infected[2] | >1000 | >1000 |
| Uninfected cell immunized[3] | <10 | <10 |
| Uninfected cell immunized[3] | <10 | <10 |

[1]Sera from inactivated Pet/FL-4 cell vaccinated cats
[2]Sera from FIV$_{Pet}$ infected cats
[3]Sera from inactivated uninfected FeT-J immunized cats

EXAMPLE 4

Immunotyping FIV Strains

Figure 6:
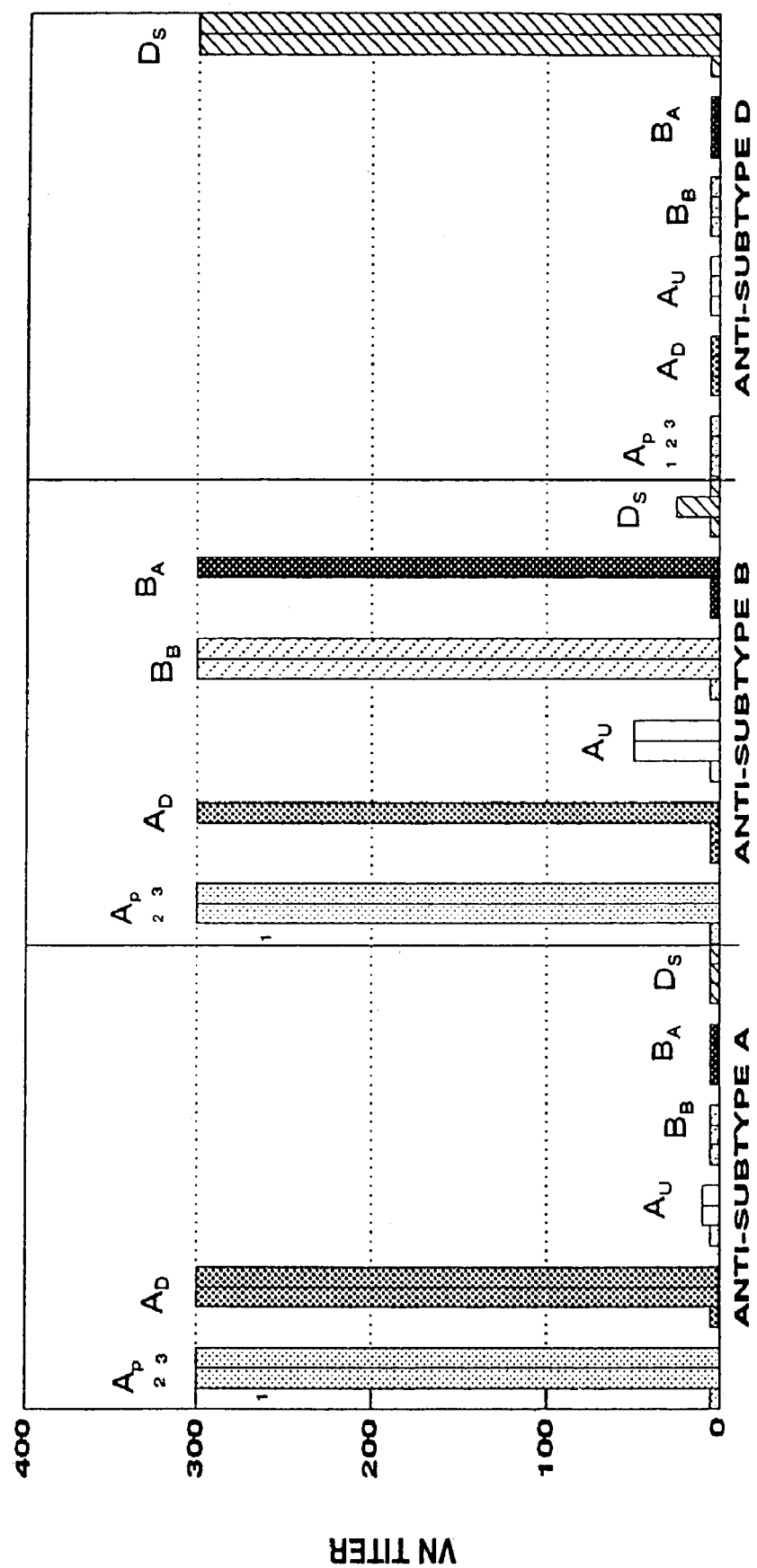

In vitro studies were performed using FeT-1C cells to assess if FIV subtype reflected FIV immunotype. Immunotyping is important for understanding the role of VN antibodies in vaccine protection. Antisera from cats infected with FIV subtype A strains (FIV$_{Pet}$, FIV$_{Dix}$, FIV$_{UK8}$), subtype B (FIV$_{Bang}$, FIV$_{Aom1}$), and subtype D (FIV$_{Shi}$) were tested for the ability to neutralize these strains in vitro using FeT-1C cells in the VN assay (FIG. 6). All of the test antisera had neutralizing activity against the corresponding homologous FIV strain. FIV$_{Pet}$, a subtype A strain, was significantly cross-neutralized by antisera from cats infected with FIV$_{Dix}$. FIV$_{Pet}$ differs from FIV$_{Dix}$ by approximately 9% at surface envelope glycoprotein (Env) regions. Anti-sera from cats infected with FIV subtype A strains cross-neutralized subtype B FIV$_{Bang}$ but did not neutralize subtype D FIV$_{Shi}$. Antisera from cats infected with subtype B and D strains only cross-neutralized other FIV strains within the homologous subtype. Further, antisera from cats infected with FIV$_{UK8}$ neutralized FIV$_{Bang}$ but did not neutralize FIV strains within subtype A. Although FIV$_{UK8}$ is classified as subtype A (Sodora et al., 1994; Rigby et al., 1993; Kakinuma et al., 1995), these results suggest that antisera to FIV$_{UK8}$ recognizes subtype B strains, but does not recognize subtype A strains, and may explain why inactivated FIV$_{Pet}$ vaccines were ineffective against FIV$_{UK8}$ and FIV$_{Shi}$ (Johnson et al., 1994). Thus, a loose correlation exists between genotype and immunotype. Although genotypic analyses allow for FIV strain classification, cross-neutralization antibody studies reflect the immunogenicity of FIV strains, which is an important parameter in broad-range humoral protection elicited by vaccines.

EXAMPLE 5

FIV Cell Tropism

The cell tropism of the FIV strains obtained from infected FeT-1C and infected FeT-J cell lines were compared to those FIV strains obtained from primary PBMC (Table 8). Two FIV isolates, FIV$_{UK8}$ and FIV$_{Bang}$, are both equally lymphotropic and macrophage-tropic, whereas FIV$_{Shi}$ is highly lymphotropic. FIV$_{Pet}$ was more lymphotropic than macrophage-tropic and its cell tropism was not significantly affected by its cell source. The macrophage-tropism of FIV$_{Bang}$ was not affected by the cell source of the virus. Since the cell tropism of the FIV strains from infected FeT-1C cell line is comparable to those produced from primary PBMC the virus grown in FeT-1C cells can be used as inoculum for VN assays and also as an in vivo inoculum for studies to evaluate therapeutic and prophylactic approaches.

TABLE 8

Cell tropism of Fly Isolates.

| | | TCID$_{50}$[a] | | | |
|---|---|---|---|---|---|
| FIV (Subtype) | FIV Source | FeT-1C | PBMC | Alveolar Macrophage | Primary Microglia |
| Petaluma (A) | PBMC | $10^4$ | $10^4$ | $10^2$ | ND |
| Petaluma (A) | FeT-1C[b] | $10^4$ | $10^4$ | $10^1$ | ND |
| Petaluma (A) | FL-4[4] | $10^4$ | $10^4$ | $10^1$ | ND |
| Dixon (A) | FeT-1C | $10^4$ | $10^3$ | $10^1$ | ND |
| UK8 (A) | PBMC | $10^2$ | $10^3$ | $10^3$ | ND |
| UK8 (A) | FeT-1C | $10^3$ | $10^3$ | $10^3$ | ND |
| Bangston (B) | PBMC | $10^3$ | $10^3$ | $10^3$ | $10^2$ |
| Bangston (B) | FeT-1C[b] | $10^3$ | $10^3$ | $10^3$ | $10^2$ |
| Bangston (B) | FeT-J[b] | $10^3$ | $10^3$ | $10^3$ | $10^2$ |
| Shizuoka (D) | PBMC | $10^2$ | $10^3$ | <1 | ND |
| Shizuoka (D) | FeT-1C[b] | $10^3$ | $10^3$ | <1 | ND |
| Shizuoka (D) | FeT-J[b] | $10^3$ | $10^3$ | ND | ND |

[a]All virus inocula were adjusted to 120,000 cpm/ml of RT activity before titration on 5 × $10^5$ cells/ml of feline T cells (FeT-1C) or primary feline cells and the results represents the highest titer of the virus harvested over 21 days of culturing.
[b]Same cells as the infected-cell vaccines.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Pedersen, Niels C., Janet K. Yamamoto, U.S. Pat. No. 5,037,753, issued Aug. 6, 1991.

Pedersen, Niels C., Janet K. Yamamoto, U.S. Pat. No. 5,118,602, issued Jun. 2, 1992.

Byars, N. E., A. C. Allison (1987) "Adjuvant formulation for use in vaccines to elicit both cell-mediated and humoral immunity," *Vaccine* 5:223-228.

Pedersen, N. C., E. W. Ho, M. L. Brown, J. K. Yamamoto (1987) "Isolation of a T-lymphotropic virus from domestic cats with an immunodeficiency-like syndrome," *Science* 235:790-793.

Yamamoto, J. K., N. C. Pedersen, E. W. Ho, T. Okuda, G. H. Theilen (1988a) "Feline immunodeficiency syndrome—a comparison between feline T-lymphotropic lentivirus and feline leukemia virus," *Leukemia*, December Supplement 2:204S-215S.

Yamamoto, J. K., E. Sparger, E. W. Ho, P. H. Andersen, T. P. O'Connor, C. P. Mandell, L. Lowenstine, N. C. Pedersen (1988) "Pathogenesis of experimentally induced feline immunodeficiency virus infection in cats," *Am. J. Vet. Res.* 49:1246-1258.

Ackley, C. D., J. K. Yamamoto, N. B. Levy, N. C. Pedersen, M. D. Cooper (1990) "Immunologic abnormalities in pathogen-free cats experimentally infected with feline immunodeficiency virus," *J. Virol.* 64:5652-5655.

Olmsted, R. A., A. K. Barnes, J. K. Yamamoto, V. M. Hirsch, R. H. Purcell, P. R. Johnson (1989) "Molecular cloning of feline immunodeficiency virus," *Proc. Nat. Acad. Sci.* 86:2448-2452.

Olmsted, R. A., V. M. Hirsch, R. H. Purcell, P. R. Johnson (1989) "Nucleotide sequence analysis of feline immunodeficiency virus: Genome organization and relationship to other lentivirus," *Proc. Natl. Acad. Sci. USA* 86:8088-8092.

Talbott, R. L., E. E. Sparger, K. M. Lovelace, W. M. Fitch, N. C. Pedersen, P. A. Luciw, J. H. Elder (1989) "Nucleotide sequence and genomic organization of feline immunodeficiency virus," *Proc. Natl. Acad. Sci. USA* 86:5743-5747.

Hosie, M. J., O. Jarrett (1990) "Serological responses of cats to feline immunodeficiency virus," *AIDS* 4:215-220.

Sodora, D. L., E. G. Shpaer, B. E. Kitchell, S. W. Dow, E. A. Hoover, J. I. Mullins (1994) "Identification of three feline immunodeficiency virus (FIV) env gene subtype and comparison of the FIV and human immunodeficiency virus type 1 evolutionary patterns," *J. Virol.* 68:2230-2238.

Rigby, M. A., E. C. Holmes, M. Pistello, A. Mackay, A. J. Leigh-Brown, J. C. Neil (1993) "Evolution of structural proteins of feline immunodeficiency virus: molecular epidemiology and evidence of selection for change," *J. Gen. Virol.* 74:425-436.

Kakinuma, S., K. Motokawa, T. Hohdatsu, J. K. Yamamoto, H. Koyama, H. Hashimoto (1995) "Nucleotide Sequence of Feline Immunodeficiency Virus: Classification of Japanese Isolates into Two Subtypes Which Are Distinct from Non-Japanese Subtypes," *Journal of Virology* 69(6):3639-3646.

Johnson, C. M., B. A. Torres, H. Koyama, J. K. Yamamoto (1994) "FIV as a model for AIDS vaccination," *AIDS Res. Hum. Retroviruses* 10:225-228.

Yamamoto, J. K., T. Hohdatsu, R. A. Olmsted, R. Pu, H. Louie, H. Zochlinski, V. Acevedo, H. M. Johnson, G. A. Soulds, M. B. Gardner (1993) "Experimental vaccine protection against homologous and heterologous strains of feline immunodeficiency virus," *J. Virol.* 67:601-605.

Yamamoto, J. K., T. Okuda, C. D. Ackley, H. Louie, H. Zochlinski, E. Pembroke, M. B. Gardner (1991a) "Experimental vaccine protection against feline immunodeficiency virus," *AIDS Res. Hum. Retroviruses* 7:911-922.

Yamamoto, J. K., C. D. Ackley, H. Zochlinski, H. Louie, E. Pembroke, M. Torten, H. Hansen, R. Munn, T. Okuda (1991b) "Development of IL-2-independent feline lymphoid cell lines chronically infected with feline immunodeficiency virus: importance for diagnostic reagents and vaccines," *Intervirol.* 32:361-375.

Murphy, F., D. W. Kingsbury (1990) "Virus Taxonomy," In *Fields Virology*, 2nd Ed., B. N. Fields, D. M. Knipe et al., eds, Raven Press, New York, Chapter 2, pp. 9-36.

Louwagie, J., F. E. McCutchan, M. Peeters, T. P. Brennan, E. Sanders-Buell, G. A. Eddy, G. van den Grosen, K. Fransen, G. M. Gershy-Damet, R. Deleys, D. S. Burke (1993) "Phylogenetic analysis of gag genes from 70 international HIV-1 isolates provides evidence for multiple genotypes," *AIDS* 7:769-780.

Rey, M. A., B. Spire, D. Dormont, F. Barre-Suinoussi, L. Montagnier, J. C. Chermann (1984) "Characterization of the RNA dependent DNA polymerase of a new human T-lymphotropic retrovirus 1(lymphadenopathy associated virus)," *Biochem. Biophys. Res. Commun.* 21:1247-1253.

Magazine, H. I, J. M. Carter, J. K, Russell, B. A. Torres, B. M. Dunn, H. M. Johnson (1988) "Use of synthetic peptides to identify and end terminal epitope on mouse gama ifn that may be involved in function," *Proc. Natl. Acad. Sci. USA* 85:1237.

Okada, S., R. Pu, E. Young, W. Stoffs, J. K. Yamamoto (1994) "Superinfection of cats with FIV Subtypes A and B," *AIDS Res. Hum. Retroviruses* 10:1739-1746.

Yamamoto, Janet K., Niels C. Pedersen, U.S. Pat. No. 5,275,813, issued Jan. 4, 1994.

Merrifield, R. B. (1963) *J. Amer. Chem. Soc.* 85:2149-2156.

I claim:

1. A vaccine composition that induces a protective immune response against two or more subtypes of FIV in an animal susceptible to infection by FIV, comprising an effective amount of an FIV immunogen to induce said immune response, wherein said FIV immunogen comprises an immunogen or immunogens from or comprising FIV subtypes A and D, or FIV subtypes A, B, and D, and wherein said immunogen or immunogens comprises at least one recombinant viral vector FIV construct that comprises a polynucleotide sequence that encodes an FIV protein that comprises an FIV envelope protein, or an immunogenic epitope thereof.

2. The vaccine composition according to claim 1, wherein said recombinant viral vector FIV construct comprises an $FIV_{env}$, or $FIV_{env-gag/pro}$ sequence.

3. The vaccine composition according to claim 1, wherein the viral vector of said recombinant viral vector FIV construct is selected from the group consisting of adenovirus, avipox virus, feline herpesvirus, vaccinia virus, canarypox virus, entomopox virus, and swinepox virus.

4. The vaccine composition according to claim 1, wherein said FIV subtypes are subtypes A and D.

5. The vaccine composition according to claim 1, wherein said FIV immunogen is or immunogens are from an FIV virus strain selected from the group consisting of $FIV_{Bang}$, $FIV_{Pet}$, and $FIV_{Shi}$.

6. The vaccine composition according to claim 1, wherein said animal is a cat.

7. The vaccine composition according to claim 1, wherein said FIV envelope protein comprises the amino acid sequence shown in SEQ ID NO: 1.

8. The vaccine composition according to claim 1, wherein said FIV protein is a chimeric protein comprising amino acid sequences of a protein from at least two different FIV subtypes.

9. The vaccine composition according to claim 1, wherein said vaccine composition further comprises an adjuvant.

10. The vaccine composition according to claim 9, wherein said adjuvant is selected from the group consisting of threonyl muramyl dipeptide, alum, complete Freund's, and incomplete Freund's.

11. The vaccine composition according to claim 1, wherein said vaccine composition is administered parenterally, orally, or nasally.

12. The vaccine composition according to claim 11, wherein said parenteral administration is by subcutaneous, intraperitoneal, or intramuscular injection.

13. The vaccine composition according to claim 1, wherein said vaccine composition comprises (a) a recombinant viral vector FIV construct and (b) at least one immunogen or immunogens selected from the group consisting of synthetic, natural or recombinant FIV envelope protein, or an immunogenic epitope thereof, cell-free whole or partial FIV virus that expresses FIV envelope protein, or an immunogenic epitope thereof, and a cell or cells infected with FIV virus that expresses FIV envelope protein, or an immunogenic epitope thereof.

14. The vaccine composition according to claim 13, wherein said cell or cells infected with FIV virus comprise a cell from one or more of the following:
   a) the cell line designated FeT-1C having ATCC accession number CRL 11968;
   b) the cell line designated FeT-J having ATCC accession number CRL 11967;
   c) the cell line designated FL-4 having ATCC accession number CRL 10772; or
   d) the cell line designated FeT-1M having ATCC accession number CRL 10775.

15. A vaccine composition that induces a protective immune response against two or more subtypes of FIV in an animal susceptible to infection by FIV, comprising an effective amount of an FIV immunogen to induce said immune response, wherein said FIV immunogen comprises an immunogen or immunogens from or comprising FIV subtypes A and D, or FIV subtypes A, B, and D, and wherein said immunogen or immunogens comprise cell-free whole or partial FIV virus that expresses FIV envelope protein, or an immunogenic epitope thereof, or a cell or cells infected with FIV virus that expresses FIV envelope protein, or an immunogenic epitope thereof, wherein said FIV virus or cell is treated by exposure to paraformaldehyde, formalin, phenol, UV light, or heat to attenuate or inactivate said FIV virus or said FIV virus infecting said cell prior to administration of said vaccine to said animal.

16. The vaccine composition according to claim 15, wherein said FIV subtypes are subtypes A and D.

17. The vaccine composition according to claim 15, wherein said FIV immunogen is or immunogens are from an FIV virus strain selected from the group consisting of $FIV_{Bang}$, $FIV_{Pet}$, and $FIV_{Shi}$.

18. The vaccine composition according to claim 15, wherein said cell is from the cell line designated FeT-1C having ATCC accession number CRL 11968 infected with FIV.

19. The vaccine composition according to claim 15, wherein said cell is from the cell line designated FeT-J having ATCC accession number CRL 11967 infected with FIV.

20. The vaccine composition according to claim 15, wherein said cell is from the cell line designated FL-4 having ATCC accession number CRL 10772 infected with FIV.

21. The vaccine composition according to claim 15, wherein said cell is from the cell line designated FeT-1M having ATCC accession number CRL 10775 infected with FIV.

22. The vaccine composition according to claim 15, wherein said cell is infected with $FIV_{Shi}$ and said cell is from a cell line designated Shi/FeT-1 C having ATCC accession number CRL 11976.

23. The vaccine composition according to claim 15, wherein said cell is infected with $FIV_{Bang}$ and said cell is from a cell line designated Bang/FeT-J having ATCC accession number CRL 11975.

24. The vaccine composition according to claim 15, wherein said animal is a cat.

25. The vaccine composition according to claim 15, wherein said vaccine composition further comprises an adjuvant.

26. The vaccine composition according to claim 25, wherein said adjuvant is selected from the group consisting of threonyl muramyl dipeptide, alum, complete Freund's, and incomplete Freund's.

27. The vaccine composition according to claim 15, wherein said vaccine composition is administered parenterally, orally, or nasally.

28. The vaccine composition according to claim 27, wherein said parenteral administration is by subcutaneous, intraperitoneal, or intramuscular injection.

29. The vaccine composition according to claim 15, wherein said FIV-infected cell is present in a dose of from about $10^6$ cells to about $10^8$ cells.

30. The vaccine composition according to claim 15, wherein said FIV-infected cell is present in a dose of from about $5\times10^6$ cells to about $7.5\times10^7$ cells.

31. The vaccine composition according to claim 15, wherein said cell-free whole or partial FIV virus is present in a dose from about 0.1 mg to about 5 mg.

32. The vaccine composition according to claim 15, wherein said cell-free whole or partial FIV virus is present in a dose from about 0.2 mg to about 2 mg.

33. The vaccine composition according to claim 15, wherein said FIV immunogen comprises (a) cells infected with FIV of a first subtype that expresses an FIV envelope protein, or an immunogenic epitope thereof, and (b) cell-free whole or partial FIV of a second subtype that expresses an FIV envelope protein, or an immunogenic epitope thereof, wherein said first and second subtype of said FIV are selected from the group consisting of A and D, and wherein said first and second subtype of FIV are not the same.

34. The vaccine composition according to claim 15, wherein said cell or cells infected with FIV virus comprise a cell from one or more of the following:
 a) the cell line designated FeT-1C having ATCC accession number CRL 11968;
 b) the cell line designated FeT-J having ATCC accession number CRL 11967;
 c) the cell line designated FL-4 having ATCC accession number CRL 10772; or
 d) the cell line designated FeT-1M having ATCC accession number CRL 10775.

35. A method for inducing a protective immune response against two or more subtypes of FIV in an animal susceptible to infection by FIV, comprising administering to said animal an effective amount of a vaccine composition comprising an FIV immunogen, wherein said FIV immunogen comprises an immunogen or immunogens from or comprising FIV subtypes A and D, or FIV subtypes A, B, and D, and wherein said immunogen or immunogens comprises at least one recombinant viral vector FIV construct that comprises a polynucleotide sequence that encodes an FIV protein that comprises an FIV envelope protein, or an immunogenic epitope thereof.

36. The method according to claim 35, wherein said recombinant viral vector FIV construct comprises an $FIV_{env}$, or $FIV_{env\text{-}gag/pro}$ sequence.

37. The method according to claim 35, wherein the viral vector of said recombinant viral vector FIV construct is selected from the group consisting of adenovirus, avipox virus, feline herpesvirus, vaccinia virus, canarypox virus, entomopox virus, and swinepox virus.

38. The method according to claim 35, wherein said FIV subtypes are subtypes A and D.

39. The method according to claim 35, wherein said FIV immunogen is or immunogens are from an FIV virus strain selected from the group consisting of $FIV_{Bang}$, $FIV_{Pet}$, and $FIV_{Shi}$.

40. The method according to claim 35, wherein said animal is a cat.

41. The method according to claim 35, wherein said FIV envelope protein comprises the amino acid sequence shown in SEQ ID NO: 1.

42. The method according to claim 35, wherein said FIV protein is a chimeric protein comprising amino acid sequences of a protein from at least two different FIV subtypes.

43. The method according to claim 35, wherein said vaccine composition further comprises an adjuvant.

44. The method according to claim 43, wherein said adjuvant is selected from the group consisting of threonyl muramyl dipeptide, alum, complete Freund's, and incomplete Freund's.

45. The method according to claim 35, wherein said vaccine composition is administered parenterally, orally, or nasally.

46. The method according to claim 45, wherein said parenteral administration is by subcutaneous, intraperitoneal, or intramuscular injection.

47. The method according to claim 35, wherein said recombinant viral vector FIV construct is administered to said animal as a primary immunization and wherein secondary immunizations comprise inactivated cells infected with FIV that expresses FIV envelope protein, or an immunogenic epitope thereof.

48. The method according to claim 35, wherein said vaccine composition comprises (a) a recombinant viral vector FIV construct and (b) at least one immunogen or immunogens selected from the group consisting of synthetic, natural or recombinant FIV envelope protein, or an immunogenic epitope thereof, cell-free whole or partial FIV virus that expresses FIV envelope protein, or an immunogenic epitope thereof, and a cell or cells infected with FIV virus that expresses FIV envelope protein, or an immunogenic epitope thereof.

49. The method according to claim 48, wherein said cell or cells infected with FIV virus comprise a cell from one or more of the following:
 a) the cell line designated FeT-1C having ATCC accession number CRL 11968;
 b) the cell line designated FeT-J having ATCC accession number CRL 11967;
 c) the cell line designated FL-4 having ATCC accession number CRL 10772; or
 d) the cell line designated FeT-1M having ATCC accession number CRL 10775.

50. A method for inducing a protective immune response against two or more subtypes of FIV in an animal susceptible to infection by FIV, comprising administering to said animal an effective amount of an FIV immunogen to induce said immune response, wherein said FIV immunogen comprises an immunogen or immunogens from or comprising FIV subtypes A and D, or FIV subtypes A, B, and D, and wherein said immunogen or immunogens comprise cell-free whole or partial FIV virus that expresses FIV envelope protein, or an immunogenic epitope thereof, or a cell or cells infected with FIV virus that expresses FIV envelope protein, or an immunogenic epitope thereof wherein said FIV virus or cell is treated by exposure to paraformaldehyde, formalin, phenol, UV light, or heat to attenuate or inactivate said FIV virus or said FIV virus infecting said cell prior to administration of said vaccine to said animal.

51. The method according to claim 50, wherein said FIV subtypes are subtypes A and D.

52. The method according to claim 50, wherein said FIV immunogen is or immunogens are from an FIV virus strain selected from the group consisting of $FIV_{Bang}$, $FIV_{Pet}$, and $FIV_{Shi}$.

53. The method according to claim 50, wherein said cell is from the cell line designated FeT-1C having ATCC accession number CRL 11968 infected with FIV.

54. The method according to claim 50, wherein said cell is from the cell line designated FeT-J having ATCC accession number CRL 11967 infected with FIV.

55. The method according to claim 50, wherein said cell is from the cell line designated FL-4 having ATCC accession number CRL 10772 infected with FIV.

56. The method according to claim 50, wherein said cell is from the cell line designated FeT-1M having ATCC accession number CRL 10775 infected with FIV.

57. The method according to claim 50, wherein said cell is infected with $FIV_{Shi}$ and said cell is from a cell line designated Shi/FeT-1C having ATCC accession number CRL 11976.

58. The method according to claim 50, wherein said cell is infected with $FIV_{Bang}$ and said cell is from a cell line designated Bang/FeT-J having ATCC accession number CRL 11975.

59. The method according to claim 50, wherein said animal is a cat.

60. The method according to claim 50, wherein said vaccine composition further comprises an adjuvant.

61. The method according to claim 60, wherein said adjuvant is selected from the group consisting of threonyl muramyl dipeptide, alum, complete Freund's, and incomplete Freund's.

62. The method according to claim 50, wherein said vaccine composition is administered parenterally, orally, or nasally.

63. The method according to claim 62, wherein said parenteral administration is by subcutaneous, intraperitoneal, or intramuscular injection.

64. The method according to claim 50, wherein said FIV-infected cell is present in a dose of from about $10^6$ cells to about $10^8$ cells.

65. The method according to claim 50, wherein said FIV-infected cell is present in a dose of from about $5 \times 10^6$ cells to about $7.5 \times 10^7$ cells.

66. The method according to claim 50, wherein said cell-free whole or partial FIV virus is present in a dose from about 0.1 mg to about 5 mg.

67. The method according to claim 50, wherein said cell-free whole or partial FIV virus is present in a dose from about 0.2 mg to about 2 mg.

68. The method according to claim 50, wherein said FIV immunogen comprises (a) cells infected with FIV of a first subtype that expresses an FIV envelope protein, or an immunogenic epitope thereof, and (b) cell-free whole or partial FIV of a second subtype that expresses FIV envelope protein, or an immunogenic epitope thereof, wherein said first and second subtype of said FIV are selected from the group consisting of A and D, and wherein said first and second subtype of FIV are not the same.

69. The method according to claim 50, wherein said cell infected with FIV is administered as a secondary immunization to said animal.

70. The method according to claim 50, wherein said cell or cells infected with FIV virus comprise a cell from one or more of the following:
  a) the cell line designated FeT-1C having ATCC accession number CRL 11968;
  b) the cell line designated FeT-J having ATCC accession number CRL 11967;
  c) the cell line designated FL-4 having ATCC accession number CRL 10772; or
  d) the cell line designated FeT-1M having ATCC accession number CRL 10775.

* * * * *

UNITED STATES PATENT AND TRADEMARK OFFICE
CERTIFICATE OF CORRECTION

PATENT NO. : 7,267,824 B2  Page 1 of 1
APPLICATION NO. : 10/408701
DATED : September 11, 2007
INVENTOR(S) : Janet K. Yamamoto It is certified that error appears in the above-identified patent and that said Letters Patent is hereby corrected as shown below:

Column 8,
Line 39 "(Yamamoto et al., 1991 a)" should read --(Yamamoto *et al.*, 1991a)--.

Column 9,
Line 8 "Lys Gin Arg Asn" should read --Lys Gln Arg Asn--.

Line 10 "peptide is: Gin Glu Leu" should read --peptide is: Gln Glu Leu--.

Column 19,
Line 9 "detectable N antibody" should read --detectable VN antibody--.

Column 20,
Line 26 (Table Heading) "Cell tropism of Fly Isolates" should read --Cell tropism of FIV Isolates--.

Column 30,
Line 43, Claim 22 "Shi/FeT-1 C" should read --Shi/FeT-1C--.

Signed and Sealed this

Thirty-first Day of March, 2009

JOHN DOLL
*Acting Director of the United States Patent and Trademark Office*